United States Patent
Minskoff et al.

(10) Patent No.: US 10,440,993 B2
(45) Date of Patent: Oct. 15, 2019

(54) HAND-HELD INHALABLE VAPOR PRODUCING DEVICE AND METHOD

(71) Applicant: InnovoSciences LLC, Ridgefield, CT (US)

(72) Inventors: Noah Mark Minskoff, Palo Alto, CA (US); Robert Stanford Magyar, Victoria (CA)

(73) Assignee: InnovoSciences LLC, Ridgefield, CT (US)

( * ) Notice: Subject to any disclaimer, the term of this patent is extended or adjusted under 35 U.S.C. 154(b) by 394 days.

(21) Appl. No.: 15/289,901

(22) Filed: Oct. 10, 2016

(65) Prior Publication Data

US 2018/0098572 A1 Apr. 12, 2018

(51) Int. Cl.
| | |
|---|---|
| *F24F 6/08* | (2006.01) |
| *A01G 13/06* | (2006.01) |
| *A24F 47/00* | (2006.01) |
| *H05B 1/02* | (2006.01) |

(52) U.S. Cl.
CPC ......... *A24F 47/008* (2013.01); *H05B 1/0244* (2013.01)

(58) Field of Classification Search
CPC ....... H03K 17/56; A24F 47/00; A24F 47/002; A24F 47/004; A24F 47/008; H05B 1/0202; H05B 1/0244; H05B 1/025
USPC .............. 392/386–406; 131/273, 193–198.2, 131/213–215.3
See application file for complete search history.

(56) References Cited

U.S. PATENT DOCUMENTS

| | | | |
|---|---|---|---|
| 4,693,868 | A | 9/1987 | Katsuda et al. |
| 6,169,852 | B1 * | 1/2001 | Liao ........................ F22B 1/284 261/142 |
| 6,578,816 | B1 | 6/2003 | Lille |
| 2006/0196518 | A1 | 9/2006 | Hon |
| 2011/0226266 | A1 | 9/2011 | Tao |
| 2011/0253798 | A1 * | 10/2011 | Tucker .................... A61L 9/037 239/13 |
| 2011/0277757 | A1 | 11/2011 | Terry et al. |
| 2012/0090630 | A1 | 4/2012 | Hon |
| 2014/0144429 | A1 | 5/2014 | Wensley et al. |
| 2014/0318560 | A1 * | 10/2014 | Hon ...................... A24F 47/002 131/329 |
| 2015/0245669 | A1 | 9/2015 | Cadieux et al. |

(Continued)

OTHER PUBLICATIONS

International Search Report and Written Opinion, International Application No. PCT/US2017/055774, dated Dec. 22, 2017, 7 pages.

(Continued)

*Primary Examiner* — Sang Y Paik
(74) *Attorney, Agent, or Firm* — Durham Jones & Pinegar, P.C., Intellectual Property Law Group

(57) ABSTRACT

Described herein are systems, devices, and methods for generating and delivering an inhalable vapor or aerosol. In some embodiments, the systems, devices, and methods described herein are used to generate and deliver a vapor or aerosol containing tobacco for use in, for example, traditional smoking or, for example, to deliver a smoking cessation therapy. In some embodiments, the systems, devices, and methods described herein are used for generating and delivering a vapor or aerosol comprising a medicament. For example, in some embodiments, the systems, devices, and methods described herein are used to deliver an inhalable medicament to the lungs of a patient.

20 Claims, 11 Drawing Sheets

(56) References Cited

U.S. PATENT DOCUMENTS

2016/0150828 A1* 6/2016 Goldstein ............ A24F 47/008
                                                                                      392/387
2016/0228658 A1     8/2016 Minskoff
2016/0262454 A1     9/2016 Sears et al.

OTHER PUBLICATIONS

International Search Report and Written Opinion, International Application No. PCT/US2017/056354, dated Dec. 14, 2017, 6 pages.

\* cited by examiner

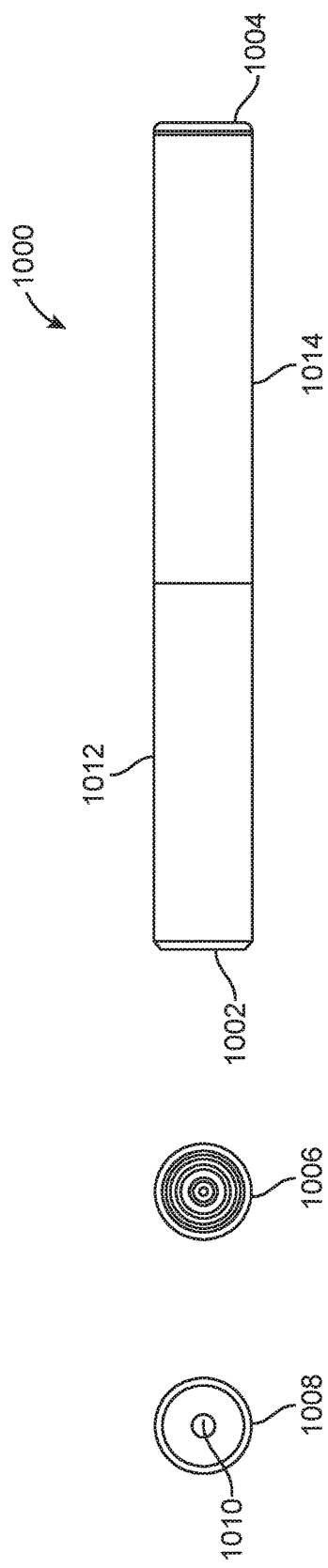

HAND-HELD INHALABLE VAPOR PRODUCING DEVICE AND METHOD

BACKGROUND

Hand-held inhalable vapor or aerosol producing devices include tobacco delivery devices such as e-cigarettes as well as inhalable medicament delivery devices.

Some traditional devices for generating inhalable vapor or aerosol are configured to heat a substance, usually in the liquid state, to a degree that the substance is converted to an inhalable vapor that a user is able to inhale.

Traditional devices are typically battery powered and may include replaceable or refillable components that allow a user to replenish the supply of a substance that is vaporized.

SUMMARY

Described herein are systems, devices, and methods for the generation of an inhalable vapor or aerosol. As described herein, a device for generating an inhalable vapor or aerosol, in some embodiments, comprises a hand-held device.

The systems, devices, and methods described herein improve on traditional hand-held inhalable vapor or aerosol producing devices in a number of ways.

Prevention of Contamination of the Generated Vapor or Aerosol

One example of how the systems, devices, and methods described herein improve on traditional hand-held inhalable vapor or aerosol producing devices is that while traditional devices create toxic bi-products that mix together with the inhalable vapor or aerosol, the systems, devices, and methods described herein prevent the contamination of the vapor or aerosol with toxic bi-products.

Traditional hand-held vapor or aerosol producing devices such as, for example, tobacco vapor or aerosol producing devices are typically configured to apply heat to the substance to be vaporized or aerosolized via a Joule heating system wherein coiled metal heating elements are heated by the passage of a current through the coils. In these traditional devices, the coils are typically inefficient at delivering heat to the substance, are commonly thermally coupled to the substance, and are typical positioned in relative proximity to the substance to be vaporized or aerosolized. The imprecision of the heating associated with Joule heating, in the traditional vapor or aerosol producing device, results in overheating of the substance to be vaporized or aerosolized, which results in the production of degradation or decomposition bi-products of the substance. In addition, the proximity of the heating coils to the substance to be heated, and the variability in temperatures reached during heating that occurs in the traditional devices results in transfer of metallic components and degradation products from the metallic coils to the substance to be vaporized or aerosolized. In, for example, devices used with tobacco products, degradation products resulting from overheating are associated with a high level of toxicity.

In contrast, the systems, devices, and methods described herein utilize more precise heat sources preventing overheating of the substance to be vaporized or aerosolized and de-couple the heat source from the substance to be vaporized or aerosolized so that any contaminants from the heat source are prevented from reaching the substance to be vaporized or aerosolized. In some embodiments of the systems, devices, and methods described herein, the heat source comprises a light energy source such as, for example, a laser. In these embodiments, a substance to be vaporized or aerosolized is positioned on a target surface and a laser produces a beam that travels to the target surface, thereby heating the substance to be vaporized or aerosolized and producing a vapor or aerosol. Because, in the systems, devices, and methods described herein, there is both a precise heat source in the form of a laser (or other light energy source) and the heat source is decoupled from the substance to be vaporized or aerosolized, there is an overall decrease in the contamination of the vapor or aerosol that is produced as described.

Control of Generated Particle Size

Another example of how the systems, devices, and methods described herein improve on traditional hand-held inhalable vapor or aerosol producing devices is that while traditional devices are not configured to change the particle size of the inhalable vapor or aerosol, the systems, devices, and methods described herein are configured so that a particle size of the inhalable vapor or aerosol may be modified. Particle size and content affect the experience of a user in that, for example, the particle size of the inhaled vapor or aerosol affects the texture and mouthfeel of the inhaled vapor or aerosol and the particle size affects how far along the airway a vapor or aerosol tends to travel. Traditional hand-held vapor or aerosol producing devices such as, for example, tobacco vapor or aerosol producing devices are typically configured to generate and deliver a vapor or aerosol particle of a consistent size. In contrast, in the systems, devices, and methods described herein, the particle size of a vapor or aerosol may be modified by a user, for example. Modifying the particle size of the delivered vapor or aerosol, for example, produces a different effect for a use when the systems, devices, and methods described herein are used to generate tobacco containing vapor or aerosol. For example, generating smaller particles of a tobacco containing vapor or aerosol more closely simulates the texture and location of deposition in the airway (smaller particles tend to travel deeper into the airway) of smoking a cigarette. For example, generating larger particles of a tobacco containing vapor or aerosol more closely simulates the texture and location of deposition in the airway (larger particles tend to not travel far into the airway) of smoking a cigar.

Hand-Held Inhalable Vapor and Aerosol Generation

Described herein is a hand-held inhalable vapor or aerosol producing device comprising: a cartridge having an opening and containing a liquid; a channel outside of the cartridge that is continuous with the opening and positioned to receive the liquid from the cartridge; a thermal valve that seals the opening in a first conformation and unseals the opening in a second conformation so that when the valve unseals the opening, the liquid is allowed to flow from the cartridge into the channel; a thermal conducting plate having a plurality of pores and in fluid communication with the channel, the thermal conducting plate configured to receive the liquid from the channel within the plurality of pores; and a heat source configured to apply heat to the thermal valve and the thermal conducting plate. In some embodiments, the cartridge contains an ejector that advances the liquid through the opening and into the channel when the opening is open. In some embodiments, the ejector travels frictionlessly within the cartridge. In some embodiments, the ejector and the cartridge are made of glass. In some embodiments, the cartridge is removable from the device. In some embodiments, the cartridge contains a bag that opens to the opening and the liquid is within the bag. In some embodiments, the bag is positioned to advance the liquid through the opening and into the channel when the opening is open. In some embodiments the cartridge is refillable by the user. In some embodiments the cartridge is intentional non-refillable or one-time-use. In some embodiments, the liquid comprises nicotine. In some embodiments, the channel is configured so that liquid advances through the channel due to capillary action. In some embodiments, the valve changes from the first conformation to the second conformation when the valve is heated by the heat source. In some embodiments, the valve comprises one or more materials that change conformation when heated. In some embodiments, the valve comprises a first metallic layer and a second metallic layer, wherein the second metallic layer is positioned to face towards the heat source, and wherein the second metallic layer has a higher coefficient of thermal expansion than the first metallic layer. In some embodiments, the valve comprises a rod that is positioned to block the opening in the first conformation, and wherein the rod is positioned to move away from the opening in the second conformation, thereby opening the opening. In some embodiments, the channel has a proximal end towards the cartridge and a distal end towards the thermal conductor, and wherein the channel widens into a reservoir at the distal end. In some embodiments, the thermal conductor is positioned to receive the liquid from the reservoir. In some embodiments, the thermal conductor comprises a metal. In some embodiments, the thermal conductor comprises titanium. In some embodiments, the thermal conductor comprises a ceramic. In some embodiments the thermal conductor is carbon based, such as carbon fiber. In some embodiments, the heat source comprises a light source. In some embodiments, the light source comprises a laser. In some embodiments, the device comprises an elliptical or parabolic or compound parabolic reflector. In some embodiments, the device comprises a Fresnel lens, a concave lens, or a combination thereof.

Described herein is a method for producing an inhalable vapor or aerosol with a device comprising a cartridge, a thermal valve, a thermal conducting plate, a heat source, and a channel positioned between the cartridge and the thermal conducting plate, the method comprising: heating the thermal valve with the heat source, thereby causing the thermal valve to change from a first conformation to a second conformation, and thereby opening an opening on the cartridge that unseals into the channel; advancing a liquid from the cartridge into the channel; receiving the liquid with the thermal conducting plate from the channel; and heating the thermal conducting plate with the liquid using the heat source, thereby heating the liquid and producing a vapor or aerosol. In some embodiments, the method comprises receiving a flow of air through an opening positioned between the heat source and the thermal conducting plate. In some embodiments, the method comprises mixing the air and the vapor or aerosol. In some embodiments, the method comprises directing the air and the vapor or aerosol that is mixed together into an impact wall, thereby preventing larger particles of vapor or aerosol from being inhaled by a user. In some embodiments, the method comprises controlling the vapor or aerosol particle size. In some embodiments, the vapor or aerosol particle size is controlled by controlling the amount of heat that is applied to the liquid by the heat source. In some embodiments, the step of advancing the liquid from the cartridge into the channel comprises advancing an ejector that is positioned in the cartridge so that the liquid is between the ejector and the opening. In some embodiments, the ejector travels frictionlessly within the cartridge. In some embodiments, the ejector and the cartridge are made of glass. In some embodiments, the method comprises removing the cartridge from the device. In some embodiments, the step of advancing the liquid from the cartridge into the channel comprises constricting a bag positioned in the cartridge so that the liquid is within the bag and the bag opens to the opening. In some embodiments, the bag is elastomeric. In some embodiments, the liquid comprises nicotine. In some embodiments, the method comprises advancing the liquid through the channel using capillary action. In some embodiments, the valve comprises one or more materials that change conformation when heated. In some embodiments, the valve comprises a first metallic layer and a second metallic layer, wherein the second metallic layer is positioned to face towards the heat source, and wherein the second metallic layer has a higher coefficient of thermal expansion than the first metallic layer. In some embodiments, the valve comprises a rod that is positioned to block the opening in the first conformation, and wherein the rod is positioned to move away from the opening in the second conformation, thereby opening the opening. In some embodiments, the channel has a proximal end towards the cartridge and a distal end towards the thermal conductor, and wherein the channel widens into a reservoir at the distal end. In some embodiments, the thermal conductor is positioned to receive the liquid from the reservoir. In some embodiments, the thermal conductor comprises a metal. In some embodiments, the thermal conductor comprises titanium. In some embodiments, the thermal conductor comprises a ceramic. In some embodiments, the thermal conductor comprises a carbon based material. In some embodiments, the heat source comprises a light source. In some embodiments, the light source comprises a laser. In some embodiments, the method comprises reflecting the laser with an elliptical reflector. In some embodiments, the method comprises collimating the laser with a Fresnel lens, a concave lens, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1D respectively show a top view, bottom view, side view, and perspective view illustrations of an exemplary embodiment of a device for the generation of an inhalable vapor or aerosol comprising a hand-held inhalable vapor or aerosol generating device.

DETAILED DESCRIPTION

Figure 1D:
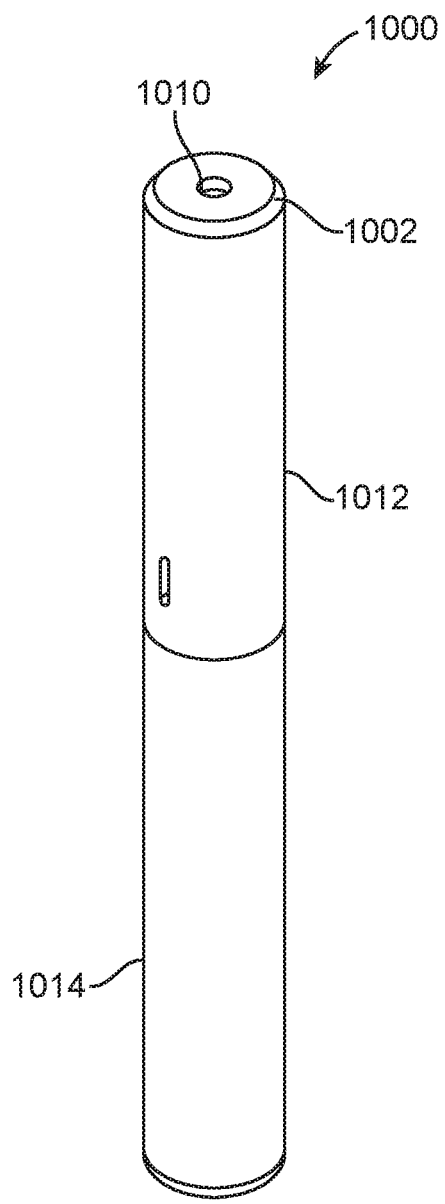

Described herein are systems, devices, and methods for generating and delivering an inhalable vapor or aerosol. In some embodiments, the systems, devices, and methods described herein are used to generate and deliver a vapor or aerosol containing tobacco, or tobacco derivatives, or nicotine or a combination of the aforementioned for use in, for example, traditional smoking or, for example, to deliver a smoking cessation therapy. In some embodiments, the systems, devices, and methods described herein are used for generating and delivering a vapor or aerosol comprising a medicament. For example, in some embodiments, the systems, devices, and methods described herein are used to deliver an inhalable medicament to the lungs of a patient.

Before describing the subject matter disclosed herein in detail, it is to be understood that the subject matter is not limited in its application to the details of construction, experiments, exemplary data, and/or the arrangement of the components set forth in the following description, or illustrated in the drawings. The subject matter described herein is capable of other variations, and therefore the variations described herein should not be taken to limit the scope of the subject matter of the description in any way. Also, it is to be understood that the phraseology and terminology employed herein is for purpose of description only and should not be regarded as limiting in any way.

As used herein, "a substance to be vaporized or aerosolized" comprises any one of a gas, a liquid, a solid, or mixture thereof and further comprises a homogenous substance or a mixture of one or more substances.

Hand-Held Simulated Smoking Device

FIGS. 1A-1D respectively show a top view, bottom view, side view, and perspective view illustrations of an exemplary embodiment of a device 1000 for the generation of an inhalable vapor or aerosol. In general, a device 1000 is sized and shaped to approximate the size and shape of a smoking article such as, for example, a traditional cigarette (or e-cigarette) or a traditional cigar.

As shown in FIG. 1A, the proximal end of the device 1000, shown in top view, comprises an outlet 1010 that is directed towards the user when the device 1000 is in use. The outlet serves as the exit for inhalable vapor or aerosol generated by the simulated smoking device 1000 that will enter the mouth and airway of a user. FIG. 1A shows a housing 1008 which is configured in some embodiments of the systems, devices, and methods described herein to contain a cartridge (not shown) of the device 1000. FIG. 1B shows a housing 1006, which in some embodiments of the systems, devices, and methods described herein contains functional components (not shown) of the device 1000.

As shown in FIG. 1C, the device 1000 has a proximal end 1002 that faces towards the user when the device 1000 is in use, and a distal end 1004 that faces away from the user when the device is in use. In some embodiments of the systems, devices, and methods described herein, a device 1000 (or other hand-held inhalable vapor generating device embodiments) comprises a cartridge containing portion 1012 that comprises housing 1008, and a primary module containing portion 1014 that comprises housing 1006. In some embodiments of the systems, devices, and methods described herein, the cartridge containing portion 1012 of the device 1000 reversibly couples with the primary module containing portion 1014 of the device 1000 so that the two components may be separated by a user, and, for example, replaced or refilled.

In some embodiments of the systems, devices, and methods described herein, a cartridge within the cartridge containing portion 1012 is configured to be replaceable. In some embodiments of the systems, devices, and methods described herein, the housing 1008 is replaceable along with the cartridge that is within it and in some embodiments of the systems, devices, and methods described herein, the housing 1008 is configured to be kept by a user while the cartridge within it is either replaced or refilled.

In some embodiments of the systems, devices, and methods described herein, a cartridge containing portion 1012 of the device 1000 and the primary module containing portion 1014 are not configured to be decoupled by a user but rather combine to form a single integrated housing.

In some embodiments of the systems, devices, and methods described herein, the size, shape, and appearance of the device 1000 approximates the size, shape, and appearance of a traditional smoking article such as, for example, a traditional cigarette, e-cigarette, or cigar.

FIG. 1D shows proximal end 1002 of the device 1000 with a beveled edge in this embodiment surrounding opening 1010. FIG. 1D shows the cartridge containing portion 1012 of the device 1000 coupled with the portion of the device 1000 that contains the primary module 1014.

Components of Exemplary Hand-Held Inhalable Vapor and Aerosol Generating Device

Figure 2:
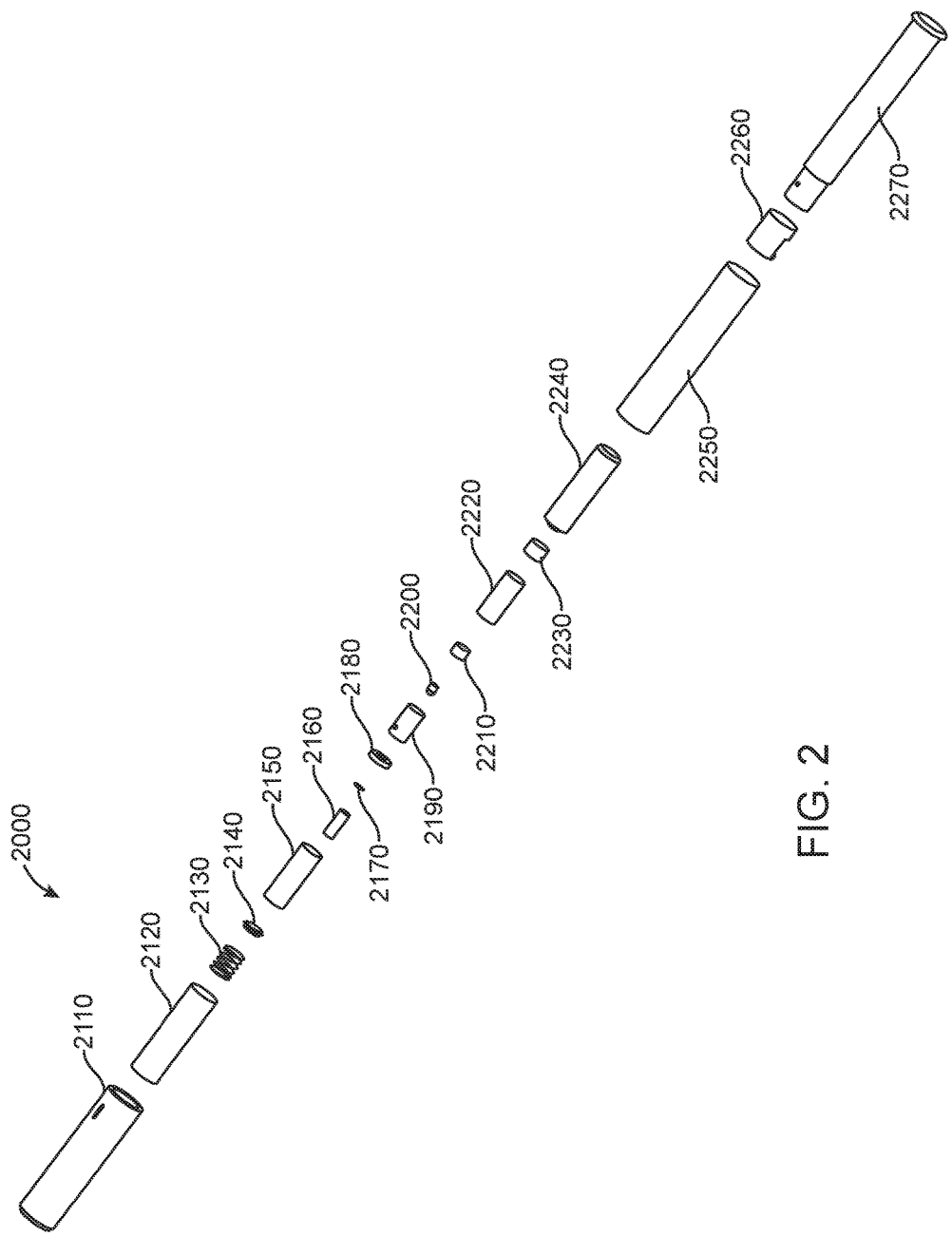
FIG. 2 shows an exploded view illustration of an exemplary embodiment of a hand-held inhalable vapor or aerosol generating device.

FIG. 2 shows an exploded view illustration of an exemplary embodiment of a device 2000, which may comprise a hand-held inhalable vapor or aerosol generating device. In some embodiments of the systems, devices, and methods described herein, the device 2000 comprises a mouthpiece 2110, a cartridge 2120, a plunger spring 2130, a plunger 2140 (or ejector), a substance to be vaporized or aerosolized 2150, a thermal valve assembly 2160, a thermal conducting plate 2170, a reservoir gasket 2180, a parabolic concentrator reflector 2190, a laser emitter 2200, a laser reflector 2210, a laser housing 2220, a computer processing unit (CPU) 2230, a battery 2240, a main housing 2250, a septum 2260, and an internal housing 2270. It should be understood, and will be in some cases explained below, that in some embodiments of the systems, devices, and methods described herein, certain of the above listed components of the exemplary device 2000 may be omitted or added to without departing from the inventive subject matter described.

A mouthpiece 2110, in some embodiments of the systems, devices, and methods described herein, includes a housing, an opening (not shown), and a hollow interior. In some embodiments of the systems, devices, and methods described herein, a mouthpiece 2110 is configured to provide or form one or more passageways through which generated vapor or aerosol travels to the mouth and airway of a user. In some embodiments, as will be explained, a passageway within a mouthpiece 2110 is configured to remove large particle contaminants from a flow of vapor or aerosol by providing impact walls that force the flow of vapor or aerosol to follow a pathway that permits travel of small particles while preventing further travel of large particles beyond the point of impact with the impact wall. A mouthpiece 2110, in some embodiments of the systems, devices, and methods described herein, contains or surrounds a cartridge 2120.

A cartridge 2120 is configured to contain a substance to either be vaporized or aerosolized 2150. In some embodiments of the systems, devices, and methods described herein, a cartridge 2120 is further configured to actively deliver the substance to be vaporized or aerosolized 2150 to one or more channels within the thermal valve assembly 2160. In some embodiments of the systems, devices, and methods described herein, the cartridge 2120 further contains a plunger 2140, and in some embodiments of the systems, devices, and methods described herein, a cartridge 2120 contains a plunger spring 2130. In some embodiments of the systems, devices, and methods described herein, a plunger 2140 is positioned within a cartridge 2120 so that the plunger 2140 is positioned proximally to the user relative to the substance to be vaporized or aerosolized 2150 when the mouthpiece 2110 of the device 2000 is oriented towards the user's mouth (i.e., the plunger 2140 is closer towards the proximal end of the device 2000 than the substance to be vaporized or aerosolized). In these embodiments, the plunger 2140 is thus positioned to push the substance to be vaporized or aerosolized 2150 out of the cartridge 2120 distally relative to a position of a user. It should be understood, however, that multiple configurations and orientations of the components within the cartridge 2120 are also suitable for use with the systems, devices, and methods described herein. For example, in some embodiments of the systems, devices, and methods described herein, the plunger 2140 is positioned distally to a user relative to the position of a substance to be vaporized or aerosolized 2150 when the mouthpiece 2110 is oriented towards the user's mouth. In some embodiments of the systems, devices, and methods described herein, for example, the cartridge is not positioned within the mouthpiece 2110 but is instead in the primary module portion of the device 2000, for example.

In some embodiments of the systems, devices, and methods described herein, a plunger 2140, within a cartridge 2120, is positioned so that the plunger 2140 abuts the substance to be vaporized or aerosolized 2150, and is further configured so that as the substance to be vaporized or aerosolized 2150 advances out of the cartridge 2120, the plunger 2140 advances in a distal direction relative to a user when the mouthpiece 2110 of the device 2000 is oriented towards a user's mouth. In some embodiments of the systems, devices, and methods described herein, the plunger 2140 is advanced within the cartridge 2120 by a plunger spring 2130. In some embodiments of the systems, devices, and methods described herein, a plunger spring 2130 is in operative communication with the plunger 2140 so that the plunger spring 2130 conveys a force to the plunger 2140, thereby causing the plunger 2140 to advance and push the substance to be vaporized or aerosolized 2150 into one or more channels within the thermal valve assembly 2160.

In some embodiments of the systems, devices, and methods described herein, the plunger spring 2130 is omitted, and one or more of the outer surface of the plunger 2140 and the inner surface of the cartridge 2120 comprises a material that creates a frictionless movement of the plunger 2140 within the cartridge 2120. For example, in some embodiments of the systems, devices, and methods described herein, the plunger 2140 has an outer surface made of glass and the cartridge 2120 has an inner surface made of glass. In some of these embodiments, having two glass surfaces, a thin layer of liquid is positioned between the glass surface of the plunger 2140 and the glass inner surface of the cartridge 2120 so that the plunger 2140 moves frictionlessly against the glass inner surface of the cartridge 2120. In some of these embodiments, having two glass surfaces, the cartridge 2120 does not include a plunger spring 2130. In some of these embodiments, having two glass surfaces, the thin layer of fluid between the plunger 2140 and the cartridge 2120 is the substance to be vaporized or aerosolized 2150. In some of these embodiments of the cartridge 2120, a plunger 2140 comprises a shuttle plug which comprises a piston-shaped body that in some embodiments has a hollow air-filled interior.

In some embodiments of the systems, devices, and methods described herein, a plunger 2140 is advanced against a substance to be vaporized or aerosolized 2150 when a user engages the mouthpiece 2110 and withdraws vapor, creating a suction force that is transmitted to the plunger 2140 through an opening in the cartridge 2120 and advances the plunger 2140 against the substance to be vaporized or aerosolized 2150, and thereby pushes the substance to be vaporized or aerosolized 2150 out of the cartridge 2120, through an opening (not shown) in the cartridge 2120, and into one or more channels (not shown) within a thermal valve assembly 2160.

In some embodiments of the systems, devices, and methods described herein, a cartridge 2120 omits the plunger spring 2130 and plunger 2140 and comprises a bag (not shown) or balloon (not shown) that advances the substance to be vaporized or aerosolized 2150 out of the one or more channels. In these embodiments, the substance to be vaporized or aerosolized 2150 is positioned within the bag or balloon so that when the bag or balloon either compresses or is advanced against the substance to be vaporized or aerosolized 2150, the substance to be vaporized or aerosolized 2150 is advanced through the opening, out of the cartridge 2120, and into one or more channels (not shown) within a thermal valve assembly 2160.

In some embodiments of the systems, devices, and methods described herein, a cartridge 2120 omits the plunger spring 2130 and plunger 2140 and comprises a reservoir of a substance to be vaporized or aerosolized 2150. In some of the systems, devices, and methods described herein, a cartridge 2120 containing a reservoir of the substance to be vaporized or aerosolized 2150 is pressurized relative to an atmospheric pressure. In some of the systems, devices, and methods described herein, a cartridge 2120 containing a reservoir of the substance to be vaporized or aerosolized 2150 is maintained at a pressure essentially equal to atmospheric pressure by an air permeable membrane that provides an airflow into the cartridge 2120 as a user applies a suction force to the cartridge 2150 by withdrawing a flow of air, vapor, and/or aerosol from the mouthpiece.

A thermal valve assembly 2160, in some embodiments of the systems, devices, and methods described herein, comprises one or more channels (not shown) and a thermal valve (not shown). One or more channels, in some embodiments of the systems, devices, and methods described herein, are continuous with an opening in the cartridge 2120 so that the one or more channels are positioned to receive a substance to be vaporized or aerosolized 2150 from the cartridge 2120. In some embodiments of the systems, devices, and methods described herein, one or more channels are configured so that they advance a liquid substance to be vaporized or aerosolized 2150 along their length through capillary action. In some embodiments of the systems, devices, and methods described herein, one or more of the channels widens at a portion of its length to form a reservoir of the substance to be vaporized or aerosolized 2150. In some embodiments, a widened portion of the one or more channels abuts a thermal conducting plate 2170.

In some embodiments of the systems, devices, and methods described herein, a thermal valve is a valve positioned within the thermal valve assembly 2160 so that when it is heated, the thermal valve unseals an opening in the cartridge 2120 that opens into the one or more channels. In these embodiments, the thermal valve is configured to change from a first conformation to a second conformation when the thermal valve is heated. Wherein, in the first conformation of the thermal valve, a component of the thermal valve, such as a rod, is positioned to block the opening of the cartridge 2120 and, in the second conformation of the thermal valve, the rod is moved away from the opening, thereby opening it and allowing the substance to be vaporized or aerosolized 2150 to be advanced into the one or more channels.

Figure 4A:
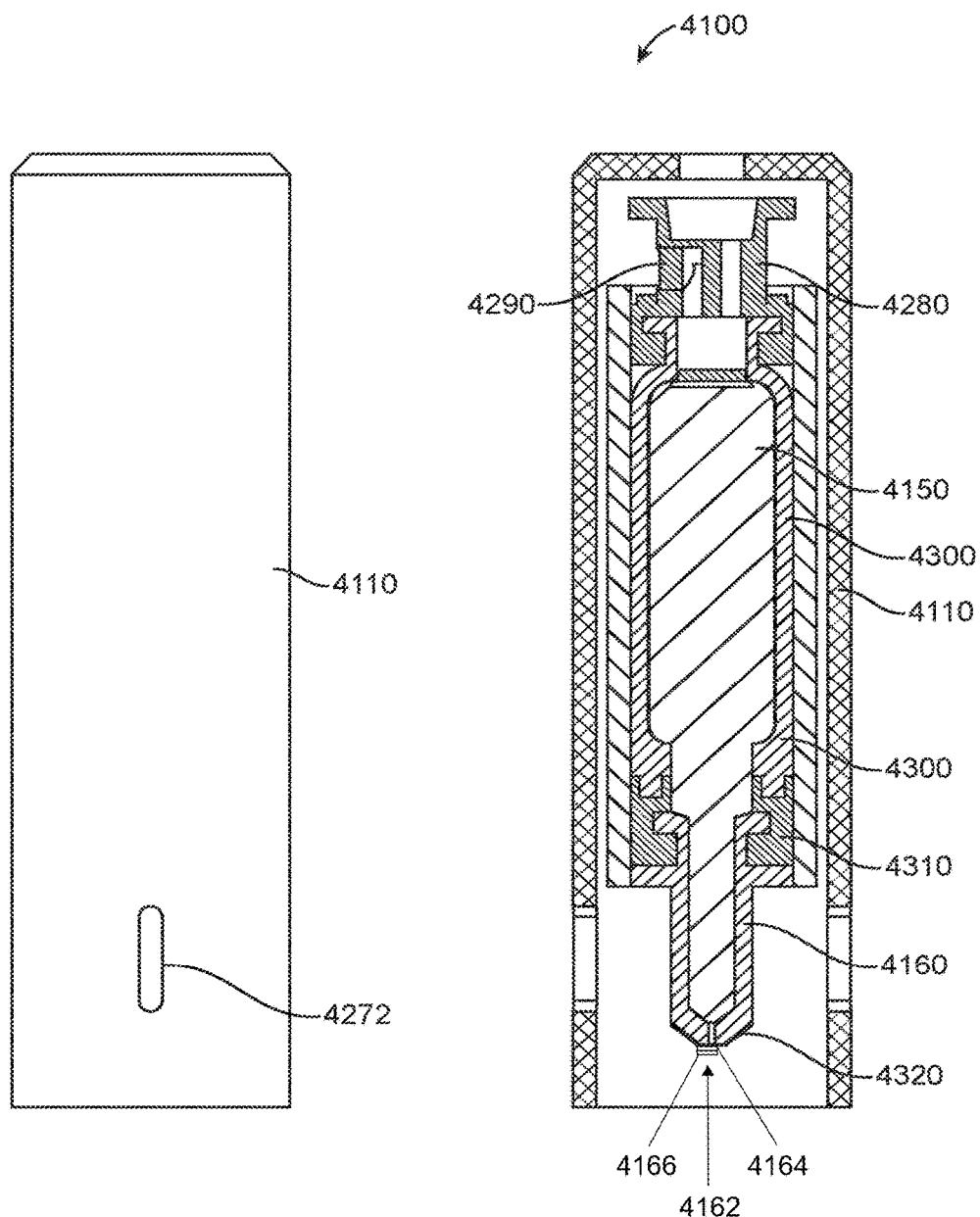
FIGS. 4A and 4B respectively show front and back cross-sectional views of an exemplary embodiment of a liquid reservoir.
Figure 4B:
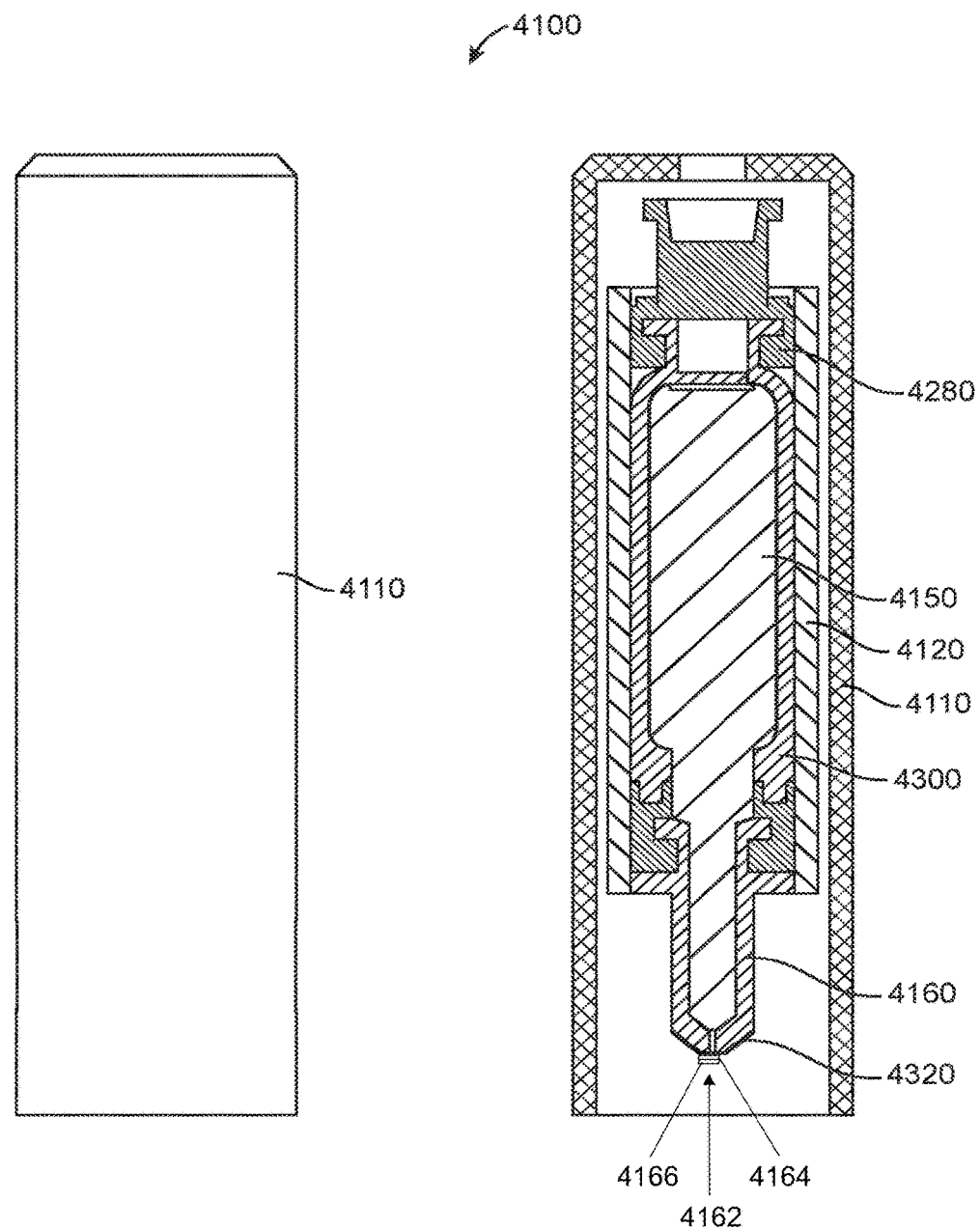
Figure 5:
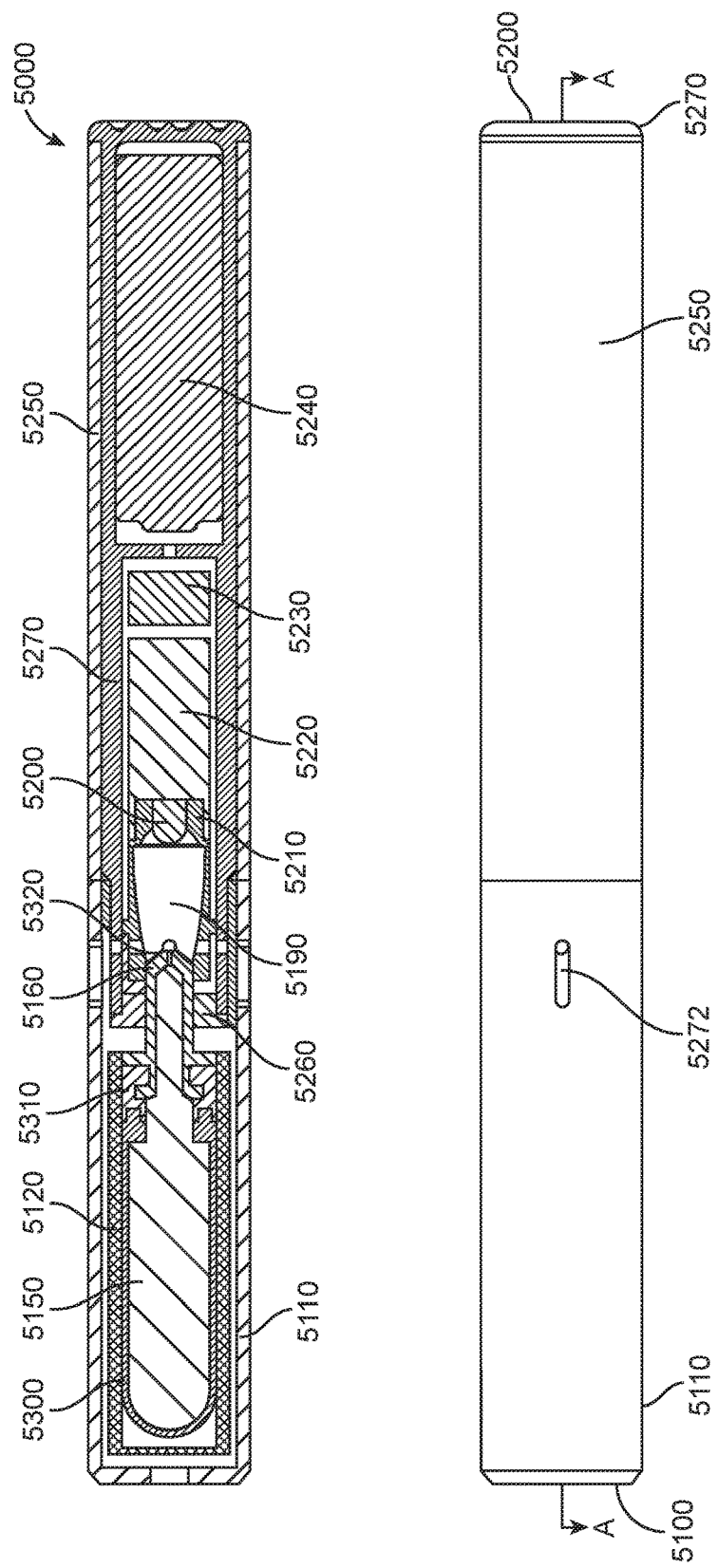
FIG. 5 shows a cross-sectional view of an exemplary embodiment of a hand-held inhalable vapor or aerosol generating device.

In some embodiments of the systems, devices, and methods described herein, a change from a first conformation of the thermal valve to a second conformation of the thermal valve is achieved through incorporation into the thermal valve of two materials each having a different coefficient of thermal expansion than the other. For example, in some embodiments of the systems, devices, and methods described herein, as depicted by FIGS. 4A and 4B, a thermal valve 4162 comprises a bimetallic portion that is composed of two different metals, each having a differing thermal coefficient of thermal expansion from the other. In these embodiments, the first metal having a first thermal coefficient of thermal expansion comprises a first layer 4164 and the second metal having a second thermal coefficient of thermal expansion comprises a second layer 4166. In these embodiments, the second layer 4166 having a higher coefficient of thermal expansion is positioned facing towards a heat source (e.g., a laser 2200, FIG. 4, etc.) so that it is closer to the heat source than the first layer 4164 having the relatively lower coefficient of thermal expansion. Thus, when the second layer 4166 having the higher coefficient of thermal expansion is heated, it tends to expand outwards and away from the first layer 4164 having the lower coefficient of thermal expansion so that the entire thermal valve 4162 tends to arc outwards towards the heat source, and thereby changing the conformation of the thermal valve 4162. In these embodiments, when a portion of the thermal valve 4162 is heated, the thermal valve 4162 arcs outward towards the heat source and changes the conformation of the thermal valve 4162. In these embodiments, the thermal valve 4162 moves within the thermal valve assembly 4160 when the thermal valve 4162 changes conformation in response to being heated, and thereby moves the component of the thermal valve 4162 that blocks the opening of the cartridge 4120 away from the opening, thereby unsealing the opening. In some embodiments of the systems, devices, and methods described herein, a first layer of a thermal valve portion that is positioned facing towards a heat source comprises copper and a second layer of the thermal valve portion comprising iron is positioned facing away from the heat source. In some embodiments of the systems, devices, and methods described herein, the surface of the bimetallic portion is coated with an IR absorbing coating. The IR absorbing coating, in some embodiments of the systems, devices, and methods described herein, is black in color and behaves as close to an ideal blackbody as possible. In these embodiments, photons from incident light from an IR heating source are absorbed by the atoms in the coating which then cause the atoms in the coating to vibrate and heat up. Acting as a thermally conductive barrier, the energy absorbed by the coating will then be transferred to the surface of the bilayer portion, causing the bilayer portion of the thermal valve 4162 to change conformation, as described above.

A thermal conducting plate 2170 is positioned, in some embodiments of the systems, devices, and methods described herein, to receive a substance to be vaporized or aerosolized 2150 from one or more channels within the thermal valve assembly 2160. In some embodiments of the systems, devices, and methods described herein, the one or more channels within the thermal valve assembly 2160 widens in diameter to form a reservoir immediately before joining with the thermal conducting plate 2170. In some embodiments of the systems, devices, and methods described herein, the thermal conducting plate 2170 comprises a porous material that is positioned to receive the substance to be vaporized or aerosolized 2150 within its pores. For example, in some embodiments of the systems, devices, and methods described herein, a substance to be vaporized or aerosolized 2150 comprises a liquid containing nicotine which is advanced from the cartridge 2120 into the one or more channels within the thermal valve assembly 2160, as described, advanced through the one or more channels by capillary action, and received into the pores of the thermal conducting plate 2170. In some embodiments of the systems, devices, and methods described herein, the substance to be vaporized or aerosolized 2150 passes through pores of the thermal conducting plate 2170 to reach a surface of the thermal conducting plate 2170 that is positioned to face a heat source. In some embodiments of the systems, devices, and methods described herein, the surface of the thermal conducting plate 2170 that faces the heat source comprises areas that are recessed so that when the substance to be vaporized of aerosolized 2150 reaches the surface, the substance to be vaporized or aerosolized 2150 enters and is contained in one or more of the recessed areas. In some embodiments of the systems, devices, and methods described herein, similar to the thermal valve of the thermal valve assembly 2160, the surface of the thermal conducting plate 2170 is coated with an IR absorbing coating to facilitate heating with an IR heating source. In some embodiments of the systems, devices, and methods described herein, a porous material that is suitable for use in the thermal conducting plate 2170 is titanium metal. In some embodiments of the systems, devices, and methods described herein, a porous material that is suitable for use in the thermal conducting plate 2170 is a ceramic. In some embodiments of the systems, devices, and methods described herein, a ceramic is composed of porous zirconia.

A reservoir gasket 2180 is positioned so that a substance to be vaporized or aerosolized 2150 does not leak around the thermal conducting plate 2170, but rather is directed to travel from the reservoir at the end of the one or more channels and into the pores of the porous material of the thermal conducting plate 2170. When heat is applied to the thermal conducting plate 2170 that contains a substance to be vaporized or aerosolized 2150, the entire thermal conducting plate 2170 heats, thereby heating the substance to be vaporized or aerosolized 2150 that is within it (i.e., within its pores and within the one or more recesses on its surface). In some embodiments of the systems, devices, and methods described herein, the substance to be vaporized or aerosolized 2150 positioned on the surface of the thermal conducting plate 2170 heats faster than that substance to be vaporized or aerosolized 2150 that is within the pores of the thermal conducting plate 2170, and as such the substance to be vaporized or aerosolized 2150 on the surface of the thermal conducting plate 2170 is vaporized or aerosolized faster than the substance within the pores of the thermal conducting plate 2170. Generally, because, in some embodiments of the systems, devices, and methods described herein, the thermal conducting plate 2170 is configured to conduct heat throughout, a substance to be vaporized or aerosolized 2150 that is in contact with a surface of the thermal conducting plate 2170 or within any of its pores will be vaporized or aerosolized when heated to the appropriate temperature by the thermal conducting plate 2170.

The thermal valve assembly 2160 and thermal conducting plate 2170 are positioned in proximity to one another within the device 2000 and positioned to be optimally heated by a heat source. Typically, in most embodiments, the thermal valve assembly 2160 and thermal conducting plate 2170 are within the cartridge containing portion of the device 2000.

In some embodiments of the systems, devices, and methods described herein, a primary module is contained within a main housing 2250 of the device 2000 and comprises a parabolic concentrator reflector 2190, a laser emitter 2200, a laser reflector 2210, a laser housing 2220, a computer processing unit (CPU) 2230, a battery 2240, a septum 2260, and an internal housing 2270.

In some embodiments of the systems, devices, and methods described herein, a heat source provides heat to at least a thermal valve and thermal conducting plate 2170 of the device 2000. In some embodiments of the systems, devices, and methods described herein, a heat source comprises a laser emitter 2200. In some embodiments of the systems, devices, and methods described herein, a heat source comprises an IR laser emitter. In some embodiments of the systems, devices, and methods described herein, the heat source comprises an LED light source. In some embodiments of the systems, devices, and methods described herein, the heat source comprises a convection or microwave heating assembly.

A laser emitter 2200 in some embodiments is within a laser housing 2220, and includes an assembly that includes reflectors and lenses that do one or more of focus, direct, and collimate the light energy that is emitted from the laser emitter 2200. In some embodiments, a laser reflector 2210 is positioned within proximity to the laser emitter 2200 and is configured to direct the emitted laser towards the thermal valve assembly 2160 and thermal conducting plate 2170. In some embodiments of the systems, devices, and methods described herein, a parabolic concentrator reflector 2190 is positioned between a laser emitter 2200 and a thermal conducting plate 2170 and is configured to focus the emitted light energy from the laser emitter 2200. In some embodiments of the systems, devices, and methods described herein, a cylindrical Fresnel lens and a concave lens (not shown) are positioned between laser emitter 2200 and the thermal valve assembly 2160 and thermal conducting plate 2170. The concave lens is configured to diverge the light energy emitted by the laser emitter 2200 and the cylindrical Fresnel lens which is positioned the closer of the two to the thermal valve assembly 2160 and thermal conducting plate 2170 is configured to collimate the light energy emitted by the laser emitter 2200. The Fresnel lens is ideal for this system because it requires less material to operate compared to other lens types. In some embodiments of the systems, devices, and methods described herein, there will also be a gold elliptical reflector (not shown) which encloses the IR absorbing portion of the target and is configured to redirect any lost emitted energy.

In some embodiments of the systems, devices, and methods described herein, a wavelength of an energy that is emitted from a heat source such as, for example, a light energy emitted from a laser emitter 2200 is matched to an optimal absorbance of a substance to be vaporized or aerosolized 2150. In some embodiments, a wavelength of an emitted energy is adjustable using, for example, CPU 2230 to modify the wavelength of a laser emitter 2200. Optimal absorbance wavelengths of a substance to be vaporized or aerosolized 2150 are determined by, for example, a standard absorbance curve.

In some of the systems, devices, and methods described herein, a device 2000 comprises a plurality of emitters, each configured to emit energy having a different wavelength. For example, in an embodiment wherein a substance to be vaporized or aerosolized 2150 comprises a mixture of a medicament and an excipient and each has a different optimal absorbance wavelength, a first emitter is set or adjusted to emit energy at a wavelength that is optimally absorbed by the medicament and a second emitter is set or adjusted to emit energy at a wavelength that is optimally absorbed by the excipient.

In some embodiments of the systems, devices, and methods described herein, the device 2000 further includes an internal housing 2270 that houses a CPU 2230, a battery 2240, and at least a portion of the other components of the primary module. In some embodiments, a septum 2260 is configured to couple the primary module with the cartridge 2120, the thermal valve assembly 2160, and the thermal conducting plate 2170. In some embodiments of the systems, devices, and methods, the internal housing comprises an opening that is positioned to be continuous with a port on the housing of the device 2000. In these embodiments, a flow of air from outside of the device 2000 may enter the device 2000 through a port in the housing of the device 2000 and then travel through an opening in the wall of the internal housing 2270 to reach the interior of the device 2000 and mix with either a vapor or aerosol that is generated by the device 2000. In these embodiments, a septum 2260 is configured to couple with the internal housing 2270 so that the opening on the wall of the internal housing 2270 is not obstructed. In some embodiments of the systems, devices, and methods described herein, a septum 2260 comprises a coupler or opening configured to receive one or more of the cartridge 2120, the thermal valve assembly 2160, and the thermal conducting plate 2170, or portions thereof.

A battery 2240 is configured to provide a power source to the heating source, CPU 2230, and any other powered components of the device 2000. In some embodiments of the systems, devices, and methods described herein, a battery 2240 is a rechargeable battery. In some embodiments of the systems, devices, and methods described herein, a battery 2240 is a lithium ion battery or a rechargeable lithium ion battery. In some embodiments of the systems, devices, and methods described herein, a battery 2240 is a lithium manganese oxide battery, a lithium manganese cobalt oxide battery, a lithium iron phosphate battery, a lithium nickel cobalt aluminum oxide battery, or a lithium titanate battery.

A CPU 2230 in some embodiments of the systems, devices, and methods described herein, includes software that controls and monitors the function of the laser emitter 2200.

A system, in some embodiments, comprises a CPU 2230 that is configured to communicate with one or more remote processors. In these system embodiments, a CPU 2230 is configured to receive commands from a remote processor and provide performance and/or usage data to a remote processor. In embodiments wherein a substance to be vaporized or aerosolized 2150 comprises a medicament, a system is configured so that a remote processor provides commands to the CPU 2230 that adjust the dosing of the vapor or aerosol generated by, for example, causing the CPU 2230 to modify the duration over which heat is applied to the substance to be vaporized or aerosolized 2150 or, for example, by causing CPU 2230 to modify the temperature of the heat that is applied to the substance to be vaporized or aerosolized 2150.

Precise heating by use of, for example, a laser emitter 2200 and CPU 2230 provides for precise temperature control of the substance to be vaporized or aerosolized 2150 in terms of both the amount of heat applied and the duration over which it is applied. Because, typically, heating for a relative higher temperature and/or longer duration generates smaller vapor or aerosol particles and heating for a relative lower temperature and/or shorter duration generates smaller vapor or aerosol particles the particle size of a generated vapor or aerosol is precisely controlled by the laser emitter 2200 in conjunction with the CPU 2230.

Substance Reservoir Cartridge Embodiments

Figure 3A:
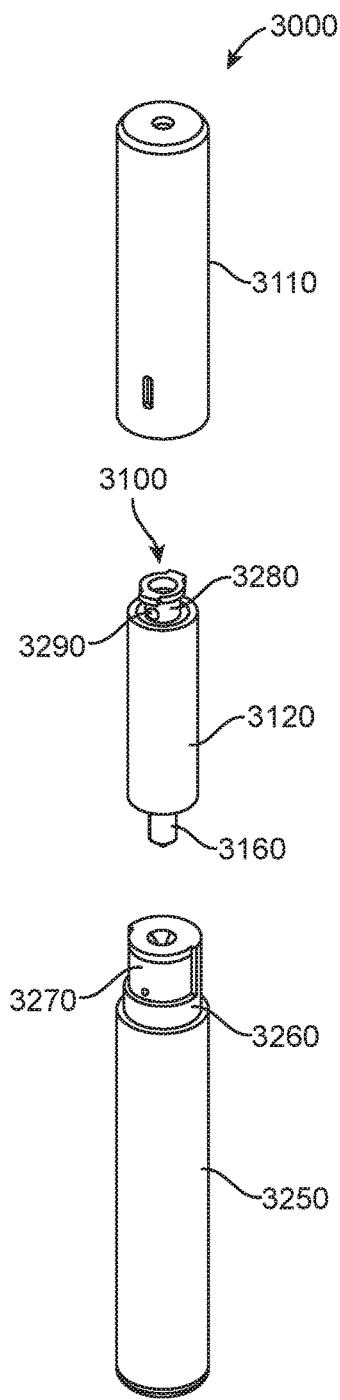
FIG. 3A shows a partially exploded view of an exemplary embodiment of a hand-held inhalable vapor generating device.
Figure 3B:
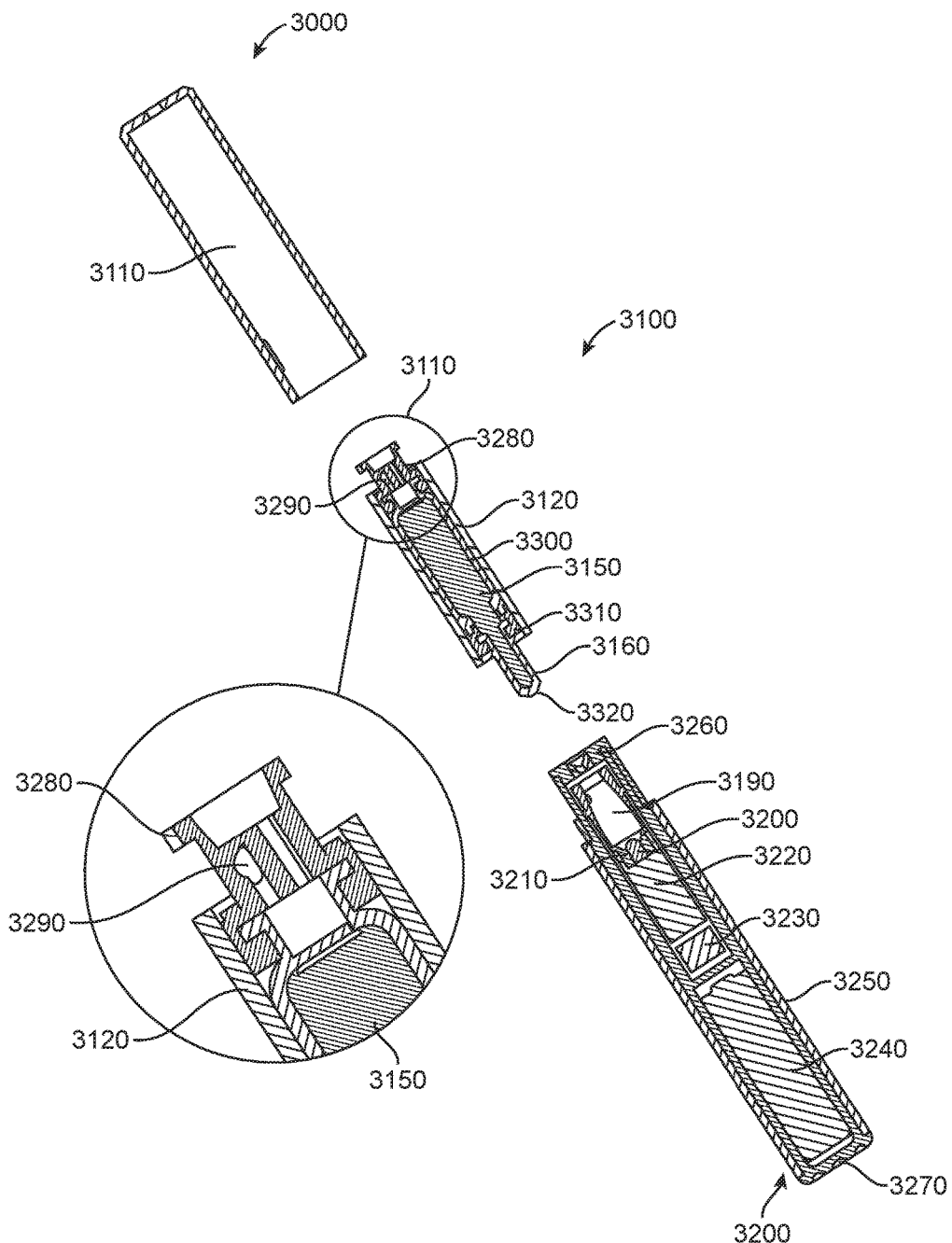
FIG. 3B shows a cross-sectional view an exemplary embodiment of a hand-held inhalable vapor generating device including an enlarged view of a portion of the substance reservoir.

FIG. 3A shows a partially exploded view of an exemplary embodiment of a device 3000, which may comprise a hand-held inhalable vapor generating device. In some embodiments of the system, devices, and methods described herein, a device 3000 as shown in FIG. 3A comprises a substance reservoir 3100, a mouthpiece 3110, a cartridge 3120, a thermal valve assembly 3160, a battery 3240, a main housing 3250, a septum 3260, an internal housing 3270, a liquid reservoir manifold 3280, and an air permeable membrane 3290. FIG. 3B shows a cross-sectional view an exemplary embodiment of a device 3000 including an enlarged view of a portion of the substance reservoir 3100. In some embodiments of the system, devices, and methods described herein, a device 3000 as shown in FIG. 3B comprises a substance reservoir 3100, a mouthpiece 3110, a cartridge 3120, a substance to be vaporized or aerosolized 3150, a thermal valve assembly 3160, a thermal conducting plate 3170, a reservoir gasket 3180, a parabolic concentrator reflector 3190, a laser emitter 3200, a laser reflector 3210, a laser housing 3220, a computer processing unit (CPU) 3230, a battery 3240, a main housing 3250, a septum 3260, an internal housing 3270, a liquid reservoir manifold 3280, and an air permeable membrane 3290.

A mouthpiece 3110, in some embodiments of the systems, devices, and methods described herein, includes a housing, an opening (not shown), and a hollow interior. In some embodiments of the systems, devices, and methods described herein, a mouthpiece 3110 is configured to provide or form one or more passageways through which generated vapor or aerosol travels to the mouth and airway of a user. In some embodiments, as will be explained, a passageway within a mouthpiece 3110 is configured to remove large particle contaminants from a flow of vapor or aerosol by providing impact walls that force the flow of vapor or aerosol to follow a pathway that permits travel of small particles while preventing further travel of large particles beyond the point of impact with the impact wall. A mouthpiece 3110, in some embodiments of the systems, devices, and methods described herein, contains or surrounds a cartridge 3120.

In some embodiments of the systems, devices, and methods described herein, a cartridge 3120 omits the plunger spring 3130 and plunger 3140 and comprises a reservoir of a substance to be vaporized or aerosolized 3150. In some of the systems, devices, and methods described herein, a cartridge 3120 containing a reservoir of the substance to be vaporized or aerosolized 3150 is pressurized relative to an atmospheric pressure. In some of the systems, devices, and methods described herein, a cartridge 3120 containing a reservoir of the substance to be vaporized or aerosolized 3150 is maintained at a pressure essentially equal to atmospheric pressure by an air permeable membrane that provides an airflow into the cartridge 3120 as a user applies a suction force to the cartridge 3150 by withdrawing a flow of air, vapor, and/or aerosol from the mouthpiece.

As shown in FIGS. 3A and 3B, in some embodiments of the systems, devices, and methods described herein, a cartridge 3120 comprises a substance reservoir 3100 that contains a substance to be vaporized or aerosolized 3150. A substance reservoir 3100 is configured to contain a substance to either be vaporized or aerosolized 3150 and to deliver the substance to be vaporized or aerosolized 3150 to one or more channels within the thermal valve assembly 3160. In some embodiments of the systems, devices, and methods described herein, the cartridge 3120 is pressurized relative to atmospheric pressure so that when an opening in the cartridge 3120 is opened, a substance to be vaporized or aerosolized 3150 is advanced due to a pressure difference between the interior of the cartridge 3120 and atmospheric pressure outside of the cartridge 3120. In some embodiment of the systems, devices, and methods described herein, the cartridge 3120 includes an elastic pressure vessel 3300 within it that is configured to maintain a pressurized environment within the cartridge 3120 as a substance to be vaporized or aerosolized 3150 advances out of the cartridge 3120, decreasing the amount of the substance to be vaporized or aerosolized 3150 within the cartridge 3120. In some embodiments of the systems, devices, and methods described herein, the cartridge 3120 has an internal pressure that is roughly equal to atmospheric pressure and includes an air permeable membrane 3290 positioned within the liquid reservoir manifold 3280. In these embodiments, the air permeable membrane 3290 communicates with the cartridge 3210 and allows air flow into the cartridge 3120, thereby maintaining atmospheric pressure within the cartridge 3120 as a liquid substance advances out and pushes air out of the cartridge 3210 with it. By maintaining atmospheric pressure within the liquid cartridge 3120 in these embodiments, the air permeable membrane 3190 allows the maintenance of continuous flow of a liquid substance to be vaporized or aerosolized 3150 out of the liquid reservoir 3120.

A thermal valve assembly 3160, in some embodiments of the systems, devices, and methods described herein, comprises one or more channels (not shown) and a thermal valve (not shown). One or more channels, in some embodiments of the systems, devices, and methods described herein, are continuous with an opening in the cartridge 3120 so that the one or more channels are positioned to receive a substance to be vaporized or aerosolized 3150 from the cartridge 3120. In some embodiments of the systems, devices, and methods described herein, one or more channels are configured so that they advance a liquid substance to be vaporized or aerosolized 3150 along their length through capillary action. In some embodiments of the systems, devices, and methods described herein, one or more of the channels widens at a portion of its length to form a reservoir of the substance to be vaporized or aerosolized 3150. In some embodiments, a widened portion of the one or more channels abuts a thermal conducting plate 3170.

In some embodiments of the systems, devices, and methods described herein, a thermal valve is a valve positioned within the thermal valve assembly 3160 so that when it is heated, the thermal valve unseals an opening in the cartridge 3120 that opens into the one or more channels. In these embodiments, the thermal valve is configured to change from a first conformation to a second conformation when the thermal valve is heated. Wherein, in the first conformation of the thermal valve, a component of the thermal valve such as, for example, a rod is positioned to block the opening of the cartridge 3120 and, in the second conformation of the thermal valve, the rod is moved away from the opening, thereby opening it and allowing the substance to be vaporized or aerosolized 3150 to be advanced into the one or more channels.

In some embodiments of the systems, devices, and methods described herein, a change from a first conformation of the thermal valve to a second conformation of the thermal valve is achieved through incorporation into the thermal valve of two materials each having a different coefficient of thermal expansion than the other. For example, in some embodiments of the systems, devices, and methods described herein, as depicted by FIGS. 4A and 4B, a thermal valve 4162 comprises a bimetallic portion that is composed of two different metals, each having a differing thermal coefficient of thermal expansion from the other. In these embodiments, the first metal having a first thermal coefficient of thermal expansion comprises a first layer 4164 and the second metal having a second thermal coefficient of thermal expansion comprises a second layer 4166. In these embodiments, the second layer 4166 having a higher coefficient of thermal expansion is positioned facing towards a heat source (e.g., a laser 2200, FIG. 4, etc.) so that it is closer to the heat source than the first layer 4164 having the relatively lower coefficient of thermal expansion. Thus, when the second layer 4166 having the higher coefficient of thermal expansion is heated, it tends to expand outwards and away from the first layer 4164 having the lower coefficient of thermal expansion so that the entire thermal valve 4162 tends to arc outwards towards the heat source, and thereby changing the conformation of the thermal valve 4162. In these embodiments, when a portion of the thermal valve 4162 is heated, the thermal valve 4162 arcs outward towards the heat source and changes the conformation of the thermal valve 4162. In these embodiments, the thermal valve 4162 moves within the thermal valve assembly 4160 when the thermal valve 4162 changes conformation in response to being heated, and thereby moves the component of the thermal valve 4162 that blocks the opening of the cartridge 4120 away from the opening, thereby unsealing the opening. In some embodiments of the systems, devices, and methods described herein, a first layer of a thermal valve portion that is positioned facing towards a heat source comprises copper and a second layer of the thermal valve portion comprising iron is positioned facing away from the heat source. In some embodiments of the systems, devices, and methods described herein, the surface of the bimetallic portion is coated with an IR absorbing coating. The IR absorbing coating, in some embodiments of the systems, devices, and methods described herein, is black in color and behaves as close to an ideal blackbody as possible. In these embodiments, photons from incident light from an IR heating source are absorbed by the atoms in the coating which then cause the atoms in the coating to vibrate and heat up. Acting as a thermally conductive barrier, the energy absorbed by the coating will then be transferred to the surface of the bilayer portion, causing the bilayer portion of the thermal valve 4162 to change conformation, as described above.

A thermal conducting plate 3170 is positioned, in some embodiments of the systems, devices, and methods described herein, to receive a substance to be vaporized or aerosolized 3150 from one or more channels within the thermal valve assembly 3160. In some embodiments of the systems, devices, and methods described herein, the one or more channels within the thermal valve assembly 3160 widens in diameter to form a reservoir immediately before joining with the thermal conducting plate 3170. In some embodiments of the systems, devices, and methods described herein, the thermal conducting plate 3170 comprises a porous material that is positioned to receive the substance to be vaporized or aerosolized 3150 within its pores. For example, in some embodiments of the systems, devices, and methods described herein, a substance to be vaporized or aeroslized 3150 comprises a liquid containing nicotine which is advanced from the cartridge 3120 into the one or more channels within the thermal valve assembly 3160, as described, advanced through the one or more channels by capillary action, and received into the pores of the thermal conducting plate 3170. In some embodiments of the systems, devices, and methods described herein, the substance to be vaporized or aerosolized 3150 passes through pores of the thermal conducting plate 3170 to reach a surface of the thermal conducting plate 3170 that is positioned to face a heat source. In some embodiments of the systems, devices, and methods described herein, the surface of the thermal conducting plate 3170 that faces the heat source comprises areas that are recessed so that when the substance to be vaporized or aerosolized 3150 reaches the surface, the substance to be vaporized or aerosolized 3150 enters and is contained in one or more of the recessed areas. In some embodiments of the systems, devices, and methods described herein, similar to the thermal valve of the thermal valve assembly 3160, the surface of the thermal conducting plate 3170 is coated with an IR absorbing coating to facilitate heating with an IR heating source. In some embodiments of the systems, devices, and methods described herein, a porous material that is suitable for use in the thermal conducting plate 3170 is titanium metal. In some embodiments of the systems, devices, and methods described herein, a porous material that is suitable for use in the thermal conducting plate 3170 is a ceramic. In some embodiments of the systems, devices, and methods described herein, a ceramic is composed of porous zirconia.

A reservoir gasket 3180 is positioned so that a substance to be vaporized or aerosolized 3150 does not leak around the thermal conducting plate 3170, but rather is directed to travel from the reservoir at the end of the one or more channels and into the pores of the porous material of the thermal conducting plate 3170. When heat is applied to the thermal conducting plate 3170 that contains a substance to be vaporized or aerosolized 3150, the entire thermal conducting plate 3170 heats, thereby heating the substance to be vaporized or aerosolized 3150 that is within it (i.e., within its pores and within the one or more recesses on its surface). In some embodiments of the systems, devices, and methods described herein, the substance to be vaporized or aerosolized 3150 positioned on the surface of the thermal conducting plate 3170 heats faster than that substance to be vaporized or aerosolized 3150 that is within the pores of the thermal conducting plate 3170, and as such the substance to be vaporized or aerosolized 3150 on the surface of the thermal conducting plate 3170 is vaporized or aerosolized faster than the substance within the pores of the thermal conducting plate 3170. Generally, because, in some embodiments of the systems, devices, and methods described herein, the thermal conducting plate 3170 is configured to conduct heat throughout, a substance to be vaporized or aerosolized 3150 that is in contact with a surface of the thermal conducting plate 3170 or within any of its pores will be vaporized or aerosolized when heated to the appropriate temperature by the thermal conducting plate 3170.

The thermal valve assembly 3160 and thermal conducting plate 3170 are positioned in proximity to one another within the device 3000 and positioned to be optimally heated by a heat source. Typically, in most embodiments, the thermal valve assembly 3160 and thermal conducting plate 3170 are within the cartridge containing portion of the device 3000.

In some embodiments of the systems, devices, and methods described herein, a primary module is contained within a main housing 3250 of the device 3000 and comprises a parabolic concentrator reflector 3190, a laser emitter 3200, a laser reflector 3210, a laser housing 3220, a computer processing unit (CPU) 3230, a battery 3240, a septum 3260, and an internal housing 3270.

In some embodiments of the systems, devices, and methods described herein, a heat source provides heat to at least a thermal valve and thermal conducting plate 3170 of the device 3000. In some embodiments of the systems, devices, and methods described herein, a heat source comprises a laser emitter 3200. In some embodiments of the systems, devices, and methods described herein, a heat source comprises an IR laser emitter. In some embodiments of the systems, devices, and methods described herein, the heat source comprises an LED light source. In some embodiments of the systems, devices, and methods described herein, the heat source comprises a convection or microwave heating assembly.

A laser emitter 3200 in some embodiments is within a laser 3220, and includes an assembly that includes reflectors and lenses that do one or more of focus, direct, and collimate the light energy that is emitted from the laser emitter 3200. In some embodiments, a laser reflector 3210 is positioned within proximity to the laser emitter 3200 and is configured to direct the emitted laser towards the thermal valve assembly 3160 and thermal conducting plate 3170. In some embodiments of the systems, devices, and methods described herein, a parabolic concentrator reflector 3190 is positioned between a laser emitter 3200 and a thermal conducting plate 3170 and is configured to focus the emitted light energy from the laser emitter 3200. In some embodiments of the systems, devices, and methods described herein, a cylindrical Fresnel lens and a concave lens (not shown) are positioned between laser emitter 3200 and the thermal valve assembly 3160 and thermal conducting plate 3170. The concave lens is configured to diverge the light energy emitted by the laser emitter 3200 and the cylindrical Fresnel lens which is positioned the closer of the two to the thermal valve assembly 3160 and thermal conducting plate 3170 is configured to collimate the light energy emitted by the laser emitter 3200. The Fresnel lens is ideal for this system because it requires less material to operate compared to other lens types. In some embodiments of the systems, devices, and methods described herein, there will also be a gold elliptical reflector (not shown) which encloses the IR absorbing portion of the target and is configured to redirect any lost emitted energy.

In some embodiments of the systems, devices, and methods described herein, a wavelength of an energy that is emitted from a heat source such as, for example, a light energy emitted from a laser emitter 3200 is matched to an optimal absorbance of a substance to be vaporized or aerosolized 3150. In some embodiments, a wavelength of an emitted energy is adjustable using, for example, CPU 3230 to modify the wavelength of a laser emitter 3200. Optimal absorbance wavelengths of a substance to be vaporized or aerosolized 3150 are determined by, for example, a standard absorbance curve.

In some of the systems, devices, and methods described herein, a device 3000 comprises a plurality of emitters, each configured to emit energy having a different wavelength. For example, in an embodiment wherein a substance to be vaporized or aerosolized 3150 comprises a mixture of a medicament and an excipient and each has a different optimal absorbance wavelength, a first emitter is set or adjusted to emit energy at a wavelength that is optimally absorbed by the medicament and a second emitter is set or adjusted to emit energy at a wavelength that is optimally absorbed by the excipient.

In some embodiments of the systems, devices, and methods described herein, the device 3000 further includes an internal housing 3270 that houses a CPU 3230, a battery 3240, and at least a portion of the other components of the primary module. In some embodiments, a septum 3260 is configured to couple the primary module with the cartridge 3120, the thermal valve assembly 3160, and the thermal conducting plate 3170. In some embodiments of the systems, devices, and methods, the internal housing 3270 comprises an opening that is positioned to be continuous with a port on the housing of the device 3000. In these embodiments, a flow of air from outside of the device 3000 may enter the device 3000 through a port in the housing of the device 3000 and then travel through an opening in the wall of the internal housing 3270 to reach the interior of the device 3000 and mix with either a vapor or aerosol that is generated by the device 3000. In these embodiments, a septum 3260 is configured to couple with the internal housing 3270 so that the opening on the wall of the internal housing 3270 is not obstructed. In some embodiments of the systems, devices, and methods described herein, a septum 3260 comprises a coupler or opening configured to receive one or more of the cartridge 2120, the thermal valve assembly 3160, and the thermal conducting plate 3170, or portions thereof.

A battery 3240 is configured to provide a power source to the heating source, CPU 3230, and any other powered components of the device 3000. In some embodiments of the systems, devices, and methods described herein, a battery 3240 is a rechargeable battery. In some embodiments of the systems, devices, and methods described herein, a battery 3240 is a lithium ion battery or a rechargeable lithium ion battery. In some embodiments of the systems, devices, and methods described herein, a battery 3240 is a lithium manganese oxide battery, a lithium manganese cobalt oxide battery, a lithium iron phosphate battery, a lithium nickel cobalt aluminum oxide battery, or a lithium titanate battery.

A CPU 3230 in some embodiments of the systems, devices, and methods described herein, includes software that controls and monitors the function of the laser emitter 3200.

A system, in some embodiments, comprises a CPU 3230 that is configured to communicate with one or more remote processors. In these system embodiments, a CPU 3230 is configured to receive commands from a remote processor and provide performance and/or usage data to a remote processor. In embodiments wherein a substance to be vaporized or aerosolized 3150 comprises a medicament, a system is configured so that a remote processor provides commands to the CPU 3230 that adjust the dosing of the vapor or aerosol generated by, for example, causing the CPU 3230 to modify the duration over which heat is applied to the substance to be vaporized or aerosolized 3150 or, for example, by causing CPU 3230 to modify the temperature of the heat that is applied to the substance to be vaporized or aerosolized 3150.

Precise heating by use of, for example, a laser emitter 3200 and CPU 3230 provides for precise temperature control of the substance to be vaporized or aerosolized 3150 in terms of both the amount of heat applied and the duration over which it is applied. Because, typically, heating for a relative higher temperature and/or longer duration generates smaller vapor or aerosol particles and heating for a relative lower temperature and/or shorter duration generates smaller vapor or aerosol particles the particle size of a generated vapor or aerosol is precisely controlled by the laser emitter 3200 in conjunction with the CPU 3230.

FIGS. 4A and 4B show front and back cross-sectional views of an exemplary embodiment of a liquid reservoir. A cartridge 4120 comprises a substance reservoir 4100 that contains a substance to be vaporized or aerosolized 4150. A substance reservoir 4100 is configured to contain a substance to either be vaporized or aerosolized 4150 and to deliver the substance to be vaporized or aerosolized 4150 to one or more channels within the thermal valve assembly 4160. In some embodiments of the systems, devices, and methods described herein, the cartridge 4120 is pressurized relative to atmospheric pressure so that when an opening in the cartridge 4120 is opened, a substance to be vaporized or aerosolized 4150 is advanced due to a pressure difference between the interior of the cartridge 4120 and atmospheric pressure outside of the cartridge 4120. In some embodiment of the systems, devices, and methods described herein, the cartridge 4120 includes an elastic pressure vessel 4400 within it that is configured to maintain a pressurized environment within the cartridge 4120 as a substance to be vaporized or aerosolized 4150 advances out of the cartridge 4120, decreasing the amount of the substance to be vaporized or aerosolized 4150 within the cartridge 4120. In some embodiments of the systems, devices, and methods described herein the cartridge 4120 has an internal pressure that is roughly equal to atmospheric pressure and includes an air permeable membrane 4290 positioned within the reservoir manifold 4280. In these embodiments, the air permeable membrane 4290 communicates with the cartridge 4120 and allows air flow into the cartridge 4120, thereby maintaining atmospheric pressure within the cartridge 4120 as a liquid substance advances out and pushes air out of the cartridge 4120 with it. By maintaining atmospheric pressure within the cartridge 4120 in these embodiments, the air permeable membrane 4190 allows the maintenance of continuous flow of a liquid substance to be vaporized or aerosolized 4150 out of the cartridge 4120.

FIG. 4A shows a port 4272 in the wall of the device 4000, which is configured to allow a flow of air to enter inside the device 4000 through the port 4272. In some embodiments of the systems, devices, and methods described herein, a port 4272 is positioned to be continuous with an opening in the wall of an internal housing which in some embodiments provides a passageway for the flow of air from outside of the device 4000 to enter the device 4000 and mix with a generated vapor or aerosol.

FIG. 5 shows a cross-sectional view of an exemplary embodiment of a device 5000, which may comprise a hand-held inhalable vapor generating device. In some embodiments of the system, devices, and methods described herein, a device 5000 comprises a proximal end 5100, a distal end 5200, a mouthpiece 5110, a cartridge 5120, a substance to be vaporized or aerosolized 5150, a thermal valve assembly 5160, a thermal conducting plate 5170, a reservoir gasket 5180, a parabolic concentrator reflector 5190, a laser emitter 5200, a laser reflector 5210, a laser housing 5220, a computer processing unit (CPU) 5230, a battery 5240, a main housing 5250, a septum 5260, an internal housing 5270, a substance reservoir 5300, and a port 5272.

A mouthpiece 5110, in some embodiments of the systems, devices, and methods described herein, includes a housing, an opening (not shown), and a hollow interior. In some embodiments of the systems, devices, and methods described herein, a mouthpiece 5110 is configured to provide or form one or more passageways through which generated vapor or aerosol travels to the mouth and airway of a user. In some embodiments, as will be explained, a passageway within a mouthpiece 5110 is configured to remove large particle contaminants from a flow of vapor or aerosol by providing impact walls that force the flow of vapor or aerosol to follow a pathway that permits travel of small particles while preventing further travel of large particles beyond the point of impact with the impact wall. A mouthpiece 5110, in some embodiments of the systems, devices, and methods described herein, contains or surrounds a cartridge 5120.

In some embodiments of the systems, devices, and methods described herein, a cartridge 5120 omits the plunger spring 5130 and plunger 5140 (or ejector) and comprises a reservoir of a substance to be vaporized or aerosolized 5150. In some of the systems, devices, and methods described herein, a cartridge 5120 containing a reservoir of the substance to be vaporized or aerosolized 5150 is pressurized relative to an atmospheric pressure. In some of the systems, devices, and methods described herein, a cartridge 5120 containing a reservoir of the substance to be vaporized or aerosolized 5150 is maintained at a pressure essentially equal to atmospheric pressure by an air permeable membrane that provides an airflow into the cartridge 5120 as a user applies a suction force to the cartridge 5120 by withdrawing a flow of air, vapor, and/or aerosol from the mouthpiece.

As shown in FIG. 5, a cartridge 5120 comprises a substance reservoir 5300 that contains a substance to be vaporized or aerosolized 5150. A substance reservoir 5300 is configured to contain a substance to either be vaporized or aerosolized 5150 and to deliver the substance to be vaporized or aerosolized 5150 to one or more channels within the thermal valve assembly 5160. In some embodiments of the systems, devices, and methods described herein, the cartridge 5120 is pressurized relative to atmospheric pressure so that when an opening in the cartridge 5120 is opened, a substance to be vaporized or aerosolized 5150 is advanced due to a pressure difference between the interior of the cartridge 5120 and atmospheric pressure outside of the cartridge 5120. In some embodiment of the systems, devices, and methods described herein, the cartridge 5120 includes an elastic pressure vessel 5500 within it that is configured to maintain a pressurized environment within the cartridge 5120 as a substance to be vaporized or aerosolized 5150 advances out of the cartridge 5120, decreasing the amount of the substance to be vaporized or aerosolized 5150 within the cartridge 5120.

A port 5272 in the wall of the device 5000, which is configured to allow a flow of air to enter inside the device 5000 through the port 5272. In some embodiments of the systems, devices, and methods described herein, a port 5272 is positioned to be continuous with an opening in the wall of an internal housing which in some embodiments provides a passageway for the flow of air from outside of the device 5000 to enter the device 5000 and mix with a generated vapor or aerosol.

A thermal valve assembly 5160, in some embodiments of the systems, devices, and methods described herein, comprises one or more channels (not shown) and a thermal valve (not shown). One or more channels, in some embodiments of the systems, devices, and methods described herein, are continuous with an opening in the cartridge 5120 so that the one or more channels are positioned to receive a substance to be vaporized or aerosolized 5150 from the cartridge 5120. In some embodiments of the systems, devices, and methods described herein, one or more channels are configured so that they advance a liquid substance to be vaporized or aerosolized 5150 along their length through capillary action. In some embodiments of the systems, devices, and methods described herein, one or more of the channels widens at a portion of its length to form a reservoir of the substance to be vaporized or aerosolized 5150. In some embodiments, a widened portion of the one or more channels abuts a thermal conducting plate 5170.

In some embodiments of the systems, devices, and methods described herein, a thermal valve is a valve positioned within the thermal valve assembly 5160 so that when it is heated, the thermal valve unseals an opening in the cartridge 5120 that opens into the one or more channels. In these embodiments, the thermal valve is configured to change from a first conformation to a second conformation when the thermal valve is heated. Wherein, in the first conformation of the thermal valve, a component of the thermal valve such as, for example, a rod is positioned to block the opening of the cartridge 5120 and, in the second conformation of the thermal valve, the rod is moved away from the opening, thereby opening it and allowing the substance to be vaporized or aerosolized 5150 to be advanced into the one or more channels.

In some embodiments of the systems, devices, and methods described herein, a change from a first conformation of the thermal valve to a second conformation of the thermal valve is achieved through incorporation into the thermal valve of two materials each having a different coefficient of thermal expansion than the other. For example, in some embodiments of the systems, devices, and methods described herein, as depicted by FIGS. 4A and 4B, a thermal valve 4162 comprises a bimetallic portion that is composed of two different metals, each having a differing thermal coefficient of thermal expansion from the other. In these embodiments, the first metal having a first thermal coefficient of thermal expansion comprises a first layer 4164 and the second metal having a second thermal coefficient of thermal expansion comprises a second layer 4166. In these embodiments, the second layer 4166 having a higher coefficient of thermal expansion is positioned facing towards a heat source (e.g., a laser 2200, FIG. 4, etc.) so that it is closer to the heat source than the first layer 4164 having the relatively lower coefficient of thermal expansion. Thus, when the second layer 4166 having the higher coefficient of thermal expansion is heated, it tends to expand outwards and away from the first layer 4164 having the lower coefficient of thermal expansion so that the entire thermal valve 4162 tends to arc outwards towards the heat source, and thereby changing the conformation of the thermal valve 4162. In these embodiments, when a portion of the thermal valve 4162 is heated, the thermal valve 4162 arcs outward towards the heat source and changes the conformation of the thermal valve 4162. In these embodiments, the thermal valve 4162 moves within the thermal valve assembly 4160 when the thermal valve 4162 changes conformation in response to being heated, and thereby moves the component of the thermal valve 4162 that blocks the opening of the cartridge 4120 away from the opening, thereby unsealing the opening. In some embodiments of the systems, devices, and methods described herein, a first layer of a thermal valve portion that is positioned facing towards a heat source comprises copper and a second layer of the thermal valve portion comprising iron is positioned facing away from the heat source. In some embodiments of the systems, devices, and methods described herein, the surface of the bimetallic portion is coated with an IR absorbing coating. The IR absorbing coating, in some embodiments of the systems, devices, and methods described herein, is black in color and behaves as close to an ideal blackbody as possible. In these embodiments, photons from incident light from an IR heating source are absorbed by the atoms in the coating which then cause the atoms in the coating to vibrate and heat up. Acting as a thermally conductive barrier, the energy absorbed by the coating will then be transferred to the surface of the bilayer portion causing the bilayer portion, of the thermal valve 5160 to change conformation, as described above.

A thermal conducting plate 5170 is positioned, in some embodiments of the systems, devices, and methods described herein, to receive a substance to be vaporized or aerosolized 5150 from one or more channels within the thermal valve assembly 5160. In some embodiments of the systems, devices, and methods described herein, the one or more channels within the thermal valve assembly 5160 widens in diameter to form a reservoir immediately before joining with the thermal conducting plate 5170. In some embodiments of the systems, devices, and methods described herein, the thermal conducting plate 5170 comprises a porous material that is positioned to receive the substance to be vaporized or aerosolized 5150 within its pores. For example, in some embodiments of the systems, devices, and methods described herein, a substance to be vaporized or aerosolized 5150 comprises a liquid containing nicotine which is advanced from the cartridge 5120 into the one or more channels within the thermal valve assembly 5160, as described, advanced through the one or more channels by capillary action, and received into the pores of the thermal conducting plate. In some embodiments of the systems, devices, and methods described herein, the substance to be vaporized or aerosolized passes through pores of the thermal conducting plate 5170 to reach a surface of the thermal conducting plate 5170 that is positioned to face a heat source. In some embodiments of the systems, devices, and methods described herein, the surface of the thermal conducting plate 5170 that faces the heat source comprises areas that are recessed so that when the substance to be vaporized or aerosolized 5150 reaches the surface, the substance to be vaporized or aerosolized 5150 enters and is contained in one or more of the recessed areas. In some embodiments of the systems, devices, and methods described herein, similar to the thermal valve of the thermal valve assembly 5160, the surface of the thermal conducting plate 5170 is coated with an IR absorbing coating to facilitate heating with an IR heating source. In some embodiments of the systems, devices, and methods described herein, a porous material that is suitable for use in the thermal conducting plate 5170 is titanium metal. In some embodiments of the systems, devices, and methods described herein, a porous material that is suitable for use in the thermal conducting plate 5170 is a ceramic. In some embodiments of the systems, devices, and methods described herein, a ceramic is composed of porous zirconia.

A reservoir gasket 5180 is positioned so that a substance to be vaporized or aerosolized 5150 does not leak around the thermal conducting plate 5170, but rather is directed to travel from the reservoir at the end of the one or more channels and into the pores of the porous material of the thermal conducting plate 5170. When heat is applied to the thermal conducting plate 5170 that contains a substance to be vaporized or aerosolized 5150, the entire thermal conducting plate 5170 heats, thereby heating the substance to be vaporized or aerosolized 5150 that is within it (i.e., within its pores and within the one or more recesses on its surface). In some embodiments of the systems, devices, and methods described herein, the substance to be vaporized or aerosolized 5150 positioned on the surface of the thermal conducting plate 5170 heats faster than that substance to be vaporized or aerosolized 5150 that is within the pores of the thermal conducting plate 5170, and as such the substance 5150 on the surface of the thermal conducting plate 5170 is vaporized or aerosolized faster than the substance within the pores of the thermal conducting plate 5170. Generally, because, in some embodiments of the systems, devices, and methods described herein, the thermal conducting plate 5170 is configured to conduct heat throughout, a substance to be vaporized or aerosolized 5150 that is in contact with a surface of the thermal conducting plate 5170 or within any of its pores will be vaporized or aerosolized when heated to the appropriate temperature by the thermal conducting plate 5170.

The thermal valve assembly 5160 and thermal conducting plate 5170 are positioned in proximity to one another within the device 5000 and positioned to be optimally heated by a heat source. Typically, in most embodiments, the thermal valve assembly 5160 and thermal conducting plate 5170 are within the cartridge containing portion of the device 5000.

In some embodiments of the systems, devices, and methods described herein, a primary module is contained within a main housing 5250 of the device 5000 and comprises a parabolic concentrator reflector 5190, a laser emitter 5200, a laser reflector 5210, a laser housing 5220, a computer processing unit (CPU) 5230, a battery 5240, a septum 5260, and an internal housing 5270.

In some embodiments of the systems, devices, and methods described herein, a heat source provides heat to at least a thermal valve and thermal conducting plate 5170 of the device 5000. In some embodiments of the systems, devices, and methods described herein, a heat source comprises a laser emitter 5200. In some embodiments of the systems, devices, and methods described herein, a heat source comprises an IR laser emitter. In some embodiments of the systems, devices, and methods described herein, the heat source comprises an LED light source. In some embodiments of the systems, devices, and methods described herein, the heat source comprises a convection or microwave heating assembly.

A laser emitter 5200 in some embodiments is within a laser housing 5220, and includes an assembly that includes reflectors and lenses that do one or more of focus, direct, and collimate the light energy that is emitted from the laser emitter 5200. In some embodiments, a laser reflector 5210 is positioned within proximity to the laser emitter 5200 and is configured to direct the emitted laser towards the thermal valve assembly 5160 and thermal conducting plate 5170. In some embodiments of the systems, devices, and methods described herein, a parabolic concentrator reflector 5190 is positioned between a laser emitter 5200 and a thermal conducting plate 5270 and is configured to focus the emitted light energy from the laser emitter 5200. In some embodiments of the systems, devices, and methods described herein, a cylindrical Fresnel lens and a concave lens (not shown) are positioned between laser emitter 5200 and the thermal valve assembly 5160 and thermal conducting plate 5170. The concave lens is configured to diverge the light energy emitted by the laser emitter 5200 and the cylindrical Fresnel lens which is positioned the closer of the two to the thermal valve assembly 5160 and thermal conducting plate 5170 is configured to collimate the light energy emitted by the laser emitter 5200. The Fresnel lens is ideal for this system because it requires less material to operate compared to other lens types. In some embodiments of the systems, devices, and methods described herein, there will also be a gold elliptical reflector (not shown) which encloses the IR absorbing portion of the target and is configured to redirect any lost emitted energy.

In some embodiments of the systems, devices, and methods described herein, a wavelength of an energy that is emitted from a heat source such as, for example, a light energy emitted from a laser emitter 5200 is matched to an optimal absorbance of a substance to be vaporized or aerosolized 5150. In some embodiments, a wavelength of an emitted energy is adjustable using, for example, CPU 5230 to modify the wavelength of a laser emitter 5200. Optimal absorbance wavelengths of a substance to be vaporized or aerosolized 5150 are determined by, for example, a standard absorbance curve.

In some of the systems, devices, and methods described herein, a device 5000 comprises a plurality of emitters, each configured to emit energy having a different wavelength. For example, in an embodiment wherein a substance to be vaporized or aerosolized 5150 comprises a mixture of a medicament and an excipient and each has a different optimal absorbance wavelength, a first emitter is set or adjusted to emit energy at a wavelength that is optimally absorbed by the medicament and a second emitter is set or adjusted to emit energy at a wavelength that is optimally absorbed by the excipient.

In some embodiments of the systems, devices, and methods described herein, the device 5000 further includes an internal housing 5270 that houses a CPU 5230, a battery 5240, and at least a portion of the other components of the primary module. In some embodiments, a septum 5260 is configured to couple the primary module with the cartridge 5120, thermal valve assembly 5160, and the thermal conducting plate 5170. In some embodiments of the systems, devices, and methods, the internal housing 5270 comprises an opening that is positioned to be continuous with a port on the housing of the device 5000. In these embodiments, a flow of air from outside of the device 5000 may enter the device 5000 through a port in the housing of the device 5000 and then travel through an opening in the wall of the internal housing 5270 to reach the interior of the device 5000 and mix with either a vapor or aerosol that is generated by the device 5000. In these embodiments, a septum 5260 is configured to couple with the internal housing 5270 so that the opening on the wall of the internal housing 5270 is not obstructed. In some embodiments of the systems, devices, and methods described herein, a septum 5260 comprises a coupler or opening configured to receive one or more of the cartridge 2120, the thermal valve assembly 5160, and the thermal conducting plate 5170, or portions thereof.

A battery 5240 is configured to provide a power source to the heating source, CPU 5230, and any other powered components of the device 5000. In some embodiments of the systems, devices, and methods described herein, a battery 5240 is a rechargeable battery. In some embodiments of the systems, devices, and methods described herein, a battery 5240 is a lithium ion battery or a rechargeable lithium ion battery. In some embodiments of the systems, devices, and methods described herein, a battery 5240 is a lithium manganese oxide battery, a lithium manganese cobalt oxide battery, a lithium iron phosphate battery, a lithium nickel cobalt aluminum oxide battery, or a lithium titanate battery.

A CPU 5230 in some embodiments of the systems, devices, and methods described herein, includes software that controls and monitors the function of the laser emitter 5200.

A system, in some embodiments, comprises a CPU 5230 that is configured to communicate with one or more remote processors. In these system embodiments, a CPU 5230 is configured to receive commands from a remote processor and provide performance and/or usage data to a remote processor. In embodiments wherein a substance to be vaporized or aerosolized 5150 comprises a medicament, a system is configured so that a remote processor provides commands to the CPU 5230 that adjust the dosing of the vapor or aerosol generated by, for example, causing the CPU 5230 to modify the duration over which heat is applied to the substance to be vaporized or aerosolized 5150 or, for example, by causing CPU 5230 to modify the temperature of the heat that is applied to the substance to be vaporized or aerosolized 5150.

Precise heating by use of, for example, a laser emitter 5200 and CPU 5230 provides for precise temperature control of the substance to be vaporized or aerosolized 5150 in terms of both the amount of heat applied and the duration over which it is applied. Because, typically, heating for a relative higher temperature and/or longer duration generates smaller vapor or aerosol particles and heating for a relative lower temperature and/or shorter duration generates smaller vapor or aerosol particles the particle size of a generated vapor or aerosol is precisely controlled by the laser emitter 5200 in conjunction with the CPU 5230.

Plunger Containing Cartridge Embodiments

Figure 6:
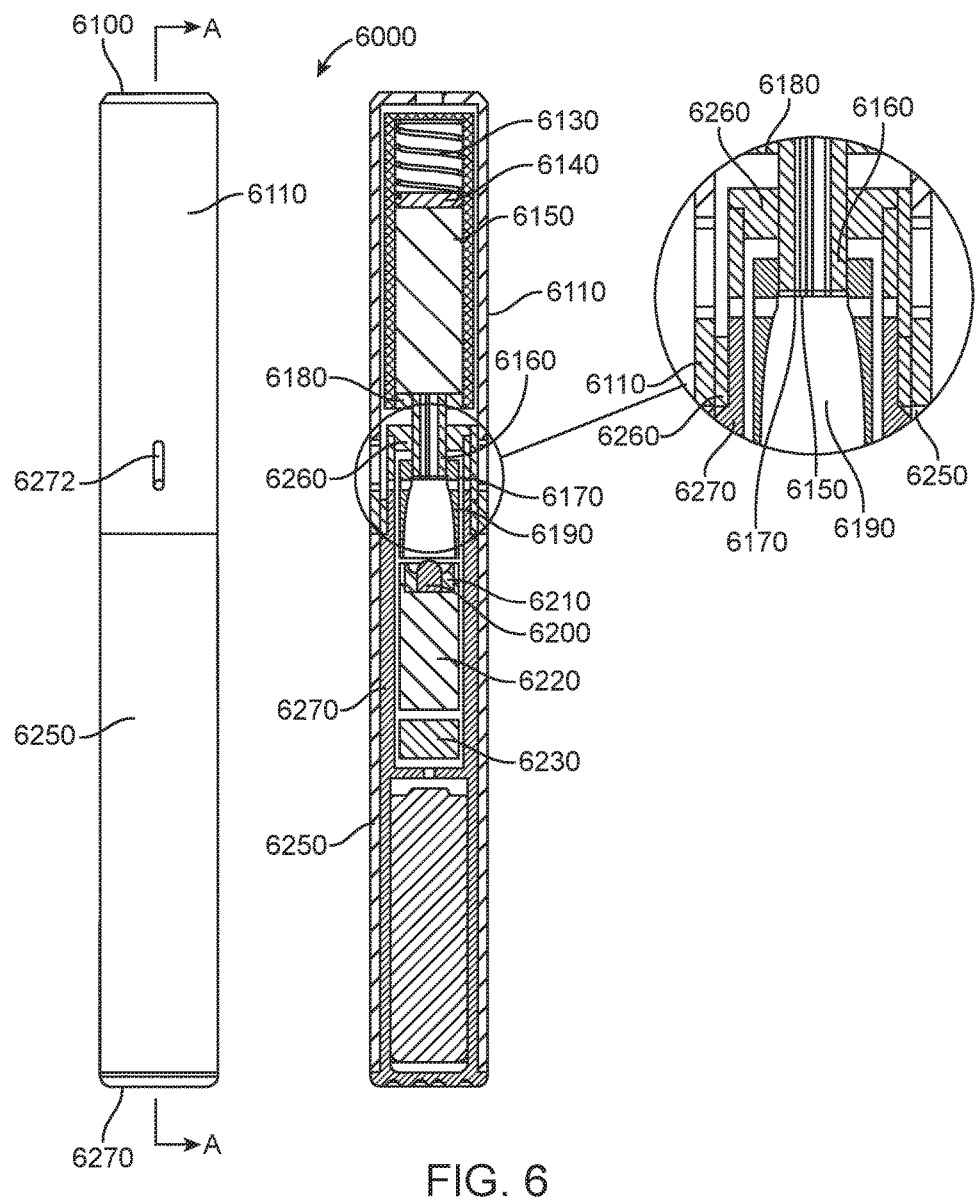
FIG. 6 shows a cross-sectional view of an exemplary embodiment of a hand-held inhalable vapor or aerosol generating device.

FIG. 6 shows a cross-sectional view of an exemplary embodiment of a device 6000, which may comprise a hand-held inhalable vapor or aerosol generating device. In some embodiments of the systems, devices, and methods described herein, a device 6000 comprises a proximal end 6100, a mouthpiece 6110, a cartridge 6120, a plunger spring 6130, a plunger 6140 (or ejector), a substance to be vaporized or aerosolized 6150, a thermal valve assembly 6160, a thermal conducting plate 6170, a reservoir gasket 6180, a parabolic concentrator reflector 6190, a laser emitter 6200, a laser reflector 6210, a laser housing 6220, a computer processing unit (CPU) 6230, a battery 6240, a main housing 6250, a septum 6260, and an internal housing 6270.

A mouthpiece 6110, in some embodiments of the systems, devices, and methods described herein, includes a housing, an opening (not shown), and a hollow interior. In some embodiments of the systems, devices, and methods described herein, a mouthpiece 6110 is configured to provide or form one or more passageways through which generated vapor or aerosol travels to the mouth and airway of a user. In some embodiments, as will be explained, a passageway within a mouthpiece 6110 is configured to remove large particle contaminants from a flow of vapor or aerosol by providing impact walls that force the flow of vapor or aerosol to follow a pathway that permits travel of small particles while preventing further travel of large particles beyond the point of impact with the impact wall. A mouthpiece 6110, in some embodiments of the systems, devices, and methods described herein, contains or surrounds a cartridge 6120.

A cartridge 6120 is configured to contain a substance to either be vaporized or aerosolized 6150. In some embodiments of the systems, devices, and methods described herein, a cartridge 6120 is further configured to actively deliver the substance to be vaporized or aerosolized 6150 to one or more channels within the thermal valve assembly 6160. In some embodiments of the systems, devices, and methods described herein, the cartridge 6120 further contains a plunger 6140, and in some embodiments of the systems, devices, and methods described herein, a cartridge 6120 contains a plunger spring 6130. In some embodiments of the systems, devices, and methods described herein, a plunger 6140 is positioned within a cartridge 6120 so that the plunger 6140 is positioned proximally to the user relative to the substance to be vaporized or aerosolized 6150 when the mouthpiece 6110 of the device 6000 is oriented towards the user's mouth (i.e., the plunger 6140 is closer towards the proximal end of the device 6000 than the substance to be vaporized or aerosolized 6150). In these embodiments, the plunger 6140 is thus positioned to push the substance to be vaporized or aerosolized 6150 out of the cartridge distally relative to a position of a user. It should be understood, however, that multiple configurations and orientations of the components within the cartridge 6120 are also suitable for use with the systems, devices, and methods described herein. For example, in some embodiments of the systems, devices, and methods described herein the plunger is positioned distally to a user relative to the position of a substance to be vaporized or aerosolized when the mouthpiece 6110 is oriented towards the user's mouth. In some embodiments of the systems, devices, and methods described herein, for example, the cartridge 6120 is not positioned within the mouthpiece 6110 but is instead in the primary module portion of the device 6000, for example.

In some embodiments of the systems, devices, and methods described herein, a plunger 6140, within a cartridge 6120, is positioned so that the plunger 6140 abuts the substance to be vaporized or aerosolized 6150, and is further configured so that as the substance to be vaporized or aerosolized 6150 advances out of the cartridge 6120, the plunger 6140 advances in a distal direction relative to a user when the mouthpiece 6110 of the device 6000 is oriented towards a user's mouth. In some embodiments of the systems, devices, and methods described herein, the plunger 6140 is advanced within the cartridge 6120 by a plunger spring 6130. In some embodiments of the systems, devices, and methods described herein, a plunger spring 6130 is in operative communication with the plunger 6140 so that the plunger spring 6130 conveys a force to the plunger 6140, thereby causing the plunger 6140 to advance and push the substance to be vaporized or aerosolized 6150 into one or more channels within the thermal valve assembly 6160.

In some embodiments of the systems, devices, and methods described herein, the plunger spring 6130 is omitted, and one or more of the outer surface of the plunger 6140 and the inner surface of the cartridge 6120 comprises a material that creates a frictionless movement of the plunger 6140 within the cartridge 6120. For example, in some embodiments of the systems, devices, and methods described herein, the plunger 6140 has an outer surface made of glass and the cartridge 6120 has an inner surface made of glass. In some of these embodiments, having two glass surfaces, a thin layer of liquid is positioned between the glass surface of the plunger 6140 and the glass inner surface of the cartridge 6120 so that the plunger 6140 moves frictionlessly against the glass inner surface of the cartridge 6120. In some of these embodiments, having two glass surfaces, the cartridge 6120 does not include a plunger spring 6130. In some of these embodiments, having two glass surfaces, the thin layer of fluid between the plunger 6140 and the cartridge 6120 is the substance to be vaporized or aerosolized 6150. In some of these embodiments of the cartridge 6120, a plunger 6140 comprises a shuttle plug which comprises a piston-shaped body that in some embodiments has a hollow air-filled interior.

In some embodiments of the systems, devices, and methods described herein, a plunger 6140 is advanced against a substance to be vaporized or aerosolized 6150 when a user engages the mouthpiece 6110 and withdraws vapor, creating a suction force that is transmitted to the plunger 6140 through an opening in the cartridge 6120 and advances the plunger 6140 against the substance to be vaporized or aerosolized 6150 and thereby pushes the substance to be vaporized or aerosolized 6150 out of the cartridge 6120, through an opening (not shown) in the cartridge 6120 and into one or more channels (not shown) within a thermal valve assembly 6160.

A thermal valve assembly 6160, in some embodiments of the systems, devices, and methods described herein, comprises one or more channels (not shown) and a thermal valve (not shown). One or more channels, in some embodiments of the systems, devices, and methods described herein, are continuous with an opening in the cartridge 6120 so that the one or more channels are positioned to receive a substance to be vaporized or aerosolized 6150 from the cartridge 6120. In some embodiments of the systems, devices, and methods described herein, one or more channels are configured so that they advance a liquid substance to be vaporized or aerosolized 6150 along their length through capillary action. In some embodiments of the systems, devices, and methods described herein, one or more of the channels widens at a portion of its length to form a reservoir of the substance to be vaporized or aerosolized 6150. In some embodiments, a widened portion of the one or more channels abuts a thermal conducting plate 6170.

In some embodiments of the systems, devices, and methods described herein, a thermal valve is a valve positioned within the thermal valve assembly 6160 so that when it is heated, the thermal valve unseals an opening in the cartridge 6120 that opens into the one or more channels. In these embodiments, the thermal valve is configured to change from a first conformation to a second conformation when the thermal valve is heated. Wherein, in the first conformation of the thermal valve, a component of the thermal valve such as, for example, a rod is positioned to block the opening of the cartridge 6120 and, in the second conformation of the thermal valve, the rod is moved away from the opening, thereby opening it and allowing the substance to be vaporized or aerosolized 6150 to be advanced into the one or more channels.

In some embodiments of the systems, devices, and methods described herein, a change from a first conformation of the thermal valve to a second conformation of the thermal valve is achieved through incorporation into the thermal valve of two materials each having a different coefficient of thermal expansion than the other. For example, in some embodiments of the systems, devices, and methods described herein, as depicted by FIGS. 4A and 4B, a thermal valve 4162 comprises a bimetallic portion that is composed of two different metals, each having a differing thermal coefficient of thermal expansion from the other. In these embodiments, the first metal having a first thermal coefficient of thermal expansion comprises a first layer 4164 and the second metal having a second thermal coefficient of thermal expansion comprises a second layer 4166. In these embodiments, the second layer 4166 having a higher coefficient of thermal expansion is positioned facing towards a heat source (e.g., a laser 2200, FIG. 4, etc.) so that it is closer to the heat source than the first layer 4164 having the relatively lower coefficient of thermal expansion. Thus, when the second layer 4166 having the higher coefficient of thermal expansion is heated, it tends to expand outwards and away from the first layer 4164 having the lower coefficient of thermal expansion so that the entire thermal valve 4162 tends to arc outwards towards the heat source, and thereby changing the conformation of the thermal valve 4162. In these embodiments, when a portion of the thermal valve 4162 is heated, the thermal valve 4162 arcs outward towards the heat source and changes the conformation of the thermal valve 4162. In these embodiments, the thermal valve 4162 moves within the thermal valve assembly 4160 when the thermal valve 4162 changes conformation in response to being heated, and thereby moves the component of the thermal valve 4162 that blocks the opening of the cartridge 4120 away from the opening, thereby unsealing the opening. In some embodiments of the systems, devices, and methods described herein, a first layer of a thermal valve portion that is positioned facing towards a heat source comprises copper and a second layer of the thermal valve portion comprising iron is positioned facing away from the heat source. In some embodiments of the systems, devices, and methods described herein, the surface of the bimetallic portion is coated with an IR absorbing coating. The IR absorbing coating, in some embodiments of the systems, devices, and methods described herein, is black in color and behaves as close to an ideal blackbody as possible. In these embodiments, photons from incident light from an IR heating source are absorbed by the atoms in the coating which then cause the atoms in the coating to vibrate and heat up. Acting as a thermally conductive barrier, the energy absorbed by the coating will then be transferred to the surface of the bilayer portion, causing the bilayer portion of the thermal valve 6160 to change conformation, as described above.

A thermal conducting plate 6170 is positioned, in some embodiments of the systems, devices, and methods described herein, to receive a substance to be vaporized or aerosolized 6150 from one or more channels within the thermal valve assembly 6160. In some embodiments of the systems, devices, and methods described herein, the one or more channels within the thermal valve assembly 6160 widens in diameter to form a reservoir immediately before joining with the thermal conducting plate 6170. In some embodiments of the systems, devices, and methods described herein, the thermal conducting plate 6170 comprises a porous material that is positioned to receive the substance to be vaporized or aerosolized 6150 within its pores. For example, in some embodiments of the systems, devices, and methods described herein, a substance to be vaporized 6150 comprises a liquid containing nicotine which is advanced from the cartridge 6120 into the one or more channels within the thermal valve assembly 6160, as described, advanced through the one or more channels by capillary action, and received into the pores of the thermal conducting plate 6170. In some embodiments of the systems, devices, and methods described herein, the substance to be vaporized or aerosolized 6150 passes through pores of the thermal conducting plate 6170 to reach a surface of the thermal conducting plate 6170 that is positioned to face a heat source. In some embodiments of the systems, devices, and methods described herein, the surface of the thermal conducting plate 6170 that faces the heat source comprises areas that are recessed so that when the substance to be vaporized or aerosolized 6150 reaches the surface, the substance to be vaporized or aerosolized 6150 enters and is contained in one or more of the recessed areas. In some embodiments of the systems, devices, and methods described herein, similar to the thermal valve of the thermal valve assembly 6160, the surface of the thermal conducting plate 6170 is coated with an IR absorbing coating to facilitate heating with an IR heating source. In some embodiments of the systems, devices, and methods described herein, a porous material that is suitable for use in the thermal conducting plate 6170 is titanium metal. In some embodiments of the systems, devices, and methods described herein, a porous material that is suitable for use in the thermal conducting plate 6170 is a ceramic. In some embodiments of the systems, devices, and methods described herein, a ceramic is composed of porous zirconia.

A reservoir gasket 6180 is positioned so that a substance to be vaporized or aerosolized 6150 does not leak around the thermal conducting plate 6170, but rather is directed to travel from the reservoir at the end of the one or more channels and into the pores of the porous material of the thermal conducting plate 6170. When heat is applied to the thermal conducting plate 6170 that contains a substance to be vaporized or aerosolized 6150, the entire thermal conducting plate 6170 heats thereby heating the substance to be vaporized or aerosolized 6150 that is within it (i.e., within its pores and within the one or more recesses on its surface). In some embodiments of the systems, devices, and methods described herein, the substance to be vaporized or aerosolized 6150 positioned on the surface of the thermal conducting plate 6170 heats faster than that substance 6150 that is within the pores of the thermal conducting plate 6170, and as such the substance 6150 on the surface of the thermal conducting plate 6170 is vaporized or aerosolized faster than the substance within the pores of the thermal conducting plate 6170. Generally, because, in some embodiments of the systems, devices, and methods described herein, the thermal conducting plate 6170 is configured to conduct heat throughout, a substance to be vaporized or aerosolized 6150 that is in contact with a surface of the thermal conducting plate 6170 or within any of its pores will be vaporized or aerosolized when heated to the appropriate temperature by the thermal conducting plate 6170.

The thermal valve assembly 6160 and thermal conducting plate 6170 are positioned in proximity to one another within the device 6000 and positioned to be optimally heated by a heat source. Typically, in most embodiments, the thermal valve assembly 6160 and thermal conducting plate 6170 are within the cartridge containing portion of the device 6000.

FIG. 6 shows an exploded view of an exemplary interface of a thermal valve assembly 6160, thermal conducting plate 6170, and a parabolic concentrator reflector 6190. As shown, a substance to be vaporized or aerosolized 6150 travels within a channel of the thermal valve assembly 6160 to a thermal conducting plate 6170 wherein the substance to be vaporized or aerosolized 6150 is deposited on a surface of the thermal conducting plate 6170 which is positioned within proximity to a parabolic concentrator reflector 6190 that is configured to collimate the emitted energy from the laser emitter 6200 onto the entire surface of the thermal conducting plate 6170.

In some embodiments of the systems, devices, and methods described herein, a primary module is contained within a main housing 6250 of the device 6000 and comprises a parabolic concentrator reflector 6190, a laser emitter 6200, a laser reflector 6210, a laser housing 6220, a computer processing unit (CPU) 6230, a battery 6240, a septum 6260, and an internal housing 6270.

In some embodiments of the systems, devices, and methods described herein, a heat source provides heat to at least a thermal valve and thermal conducting plate 6170 of the device 6000. In some embodiments of the systems, devices, and methods described herein, a heat source comprises a laser emitter 6200. In some embodiments of the systems, devices, and methods described herein, a heat source comprises an IR laser emitter. In some embodiments of the systems, devices, and methods described herein, the heat source comprises an LED light source. In some embodiments of the systems, devices, and methods described herein, the heat source comprises a convection or microwave heating assembly.

A laser emitter 6200 in some embodiments is within a laser housing 6220, and includes an assembly that includes reflectors and lenses that do one or more of focus, direct, and collimate the light energy that is emitted from the laser emitter 6200. In some embodiments, a laser reflector 6210 is positioned within proximity to the laser emitter 6200 and is configured to direct the emitted laser towards the thermal valve assembly 6160 and thermal conducting plate 6170. In some embodiments of the systems, devices, and methods described herein, a parabolic concentrator reflector 6190 is positioned between a laser emitter 6200 and a thermal conducting plate 6170 and is configured to focus the emitted light energy from the laser emitter 6200. In some embodiments of the systems, devices, and methods described herein, a cylindrical Fresnel lens and a concave lens (not shown) are positioned between laser emitter 6200 and the thermal valve assembly 6160 and thermal conducting plate 6170. The concave lens is configured to diverge the light energy emitted by the laser emitter 6200 and the cylindrical Fresnel lens which is positioned the closer of the two to the thermal valve assembly 6120 and thermal conducting plate 6170 is configured to collimate the light energy emitted by the laser emitter 6200. The Fresnel lens is ideal for this system because it requires less material to operate compared to other lens types. In some embodiments of the systems, devices, and methods described herein, there will also be a gold elliptical reflector (not shown) which encloses the IR absorbing portion of the target and is configured to redirect any lost emitted energy.

In some embodiments of the systems, devices, and methods described herein, a wavelength of an energy that is emitted from a heat source such as, for example, a light energy emitted from a laser emitter 6200 is matched to an optimal absorbance of a substance to be vaporized or aerosolized 6150. In some embodiments, a wavelength of an emitted energy is adjustable using, for example, CPU 6230 to modify the wavelength of a laser emitter 6200. Optimal absorbance wavelengths of a substance to be vaporized or aerosolized 6150 are determined by, for example, a standard absorbance curve.

In some of the systems, devices, and methods described herein, a device 6000 comprises a plurality of emitters, each configured to emit energy having a different wavelength. For example, in an embodiment wherein a substance to be vaporized or aerosolized 6150 comprises a mixture of a medicament and an excipient and each has a different optimal absorbance wavelength, a first emitter is set or adjusted to emit energy at a wavelength that is optimally absorbed by the medicament and a second emitter is set or adjusted to emit energy at a wavelength that is optimally absorbed by the excipient.

In some embodiments of the systems, devices, and methods described herein, the device 6000 further includes an internal housing 6270 that houses a CPU 6230, a battery 6240, and at least a portion of the other components of the primary module. In some embodiments, a septum 6260 is configured to couple the primary module with the cartridge 6120, the thermal valve assembly 6160, and the thermal conducting plate 6170. In some embodiments of the systems, devices, and methods, the internal housing 6270 comprises an opening that is positioned to be continuous with a port on the housing of the device 6000. In these embodiments, a flow of air from outside of the device 6000 may enter the device 6000 through a port in the housing of the device 6000 and then travel through an opening in the wall of the internal housing 6270 to reach the interior of the device 6000 and mix with either a vapor or aerosol that is generated by the device 6000. In these embodiments, a septum 6260 is configured to couple with the internal housing 6270 so that the opening on the wall of the internal housing 6270 is not obstructed. In some embodiments of the systems, devices, and methods described herein, a septum 6260 comprises a coupler or opening configured to receive one or more of the cartridge 6120, the thermal valve assembly 6160, and the thermal conducting plate 6170, or portions thereof.

A battery 6240 is configured to provide a power source to the heating source, CPU 6230, and any other powered components of the device 6000. In some embodiments of the systems, devices, and methods described herein, a battery 6240 is a rechargeable battery. In some embodiments of the systems, devices, and methods described herein, a battery 6240 is a lithium ion battery or a rechargeable lithium ion battery. In some embodiments of the systems, devices, and methods described herein, a battery 6240 is a lithium manganese oxide battery, a lithium manganese cobalt oxide battery, a lithium iron phosphate battery, a lithium nickel cobalt aluminum oxide battery, or a lithium titanate battery.

A CPU 6230 in some embodiments of the systems, devices, and methods described herein, includes software that controls and monitors the function of the laser emitter 6200.

A system, in some embodiments, comprises a CPU 6230 that is configured to communicate with one or more remote processors. In these system embodiments, a CPU 6230 is configured to receive commands from a remote processor and provide performance and/or usage data to a remote processor. In embodiments wherein a substance to be vaporized or aerosolized 6150 comprises a medicament, a system is configured so that a remote processor provides commands to the CPU 6230 that adjust the dosing of the vapor or aerosol generated by, for example, causing the CPU 6230 to modify the duration over which heat is applied to the substance to be vaporized or aerosolized 6150 or, for example, by causing CPU 6230 to modify the temperature of the heat that is applied to the substance to be vaporized or aerosolized 6150.

Precise heating by use of, for example, a laser emitter 6200 and CPU 6230 provides for precise temperature control of the substance to be vaporized or aerosolized 6150 in terms of both the amount of heat applied and the duration over which it is applied. Because, typically, heating for a relative higher temperature and/or longer duration generates smaller vapor or aerosol particles and heating for a relative lower temperature and/or shorter duration generates smaller vapor or aerosol particles the particle size of a generated vapor or aerosol is precisely controlled by the laser emitter 6200 in conjunction with the CPU 6230.

Figure 7:
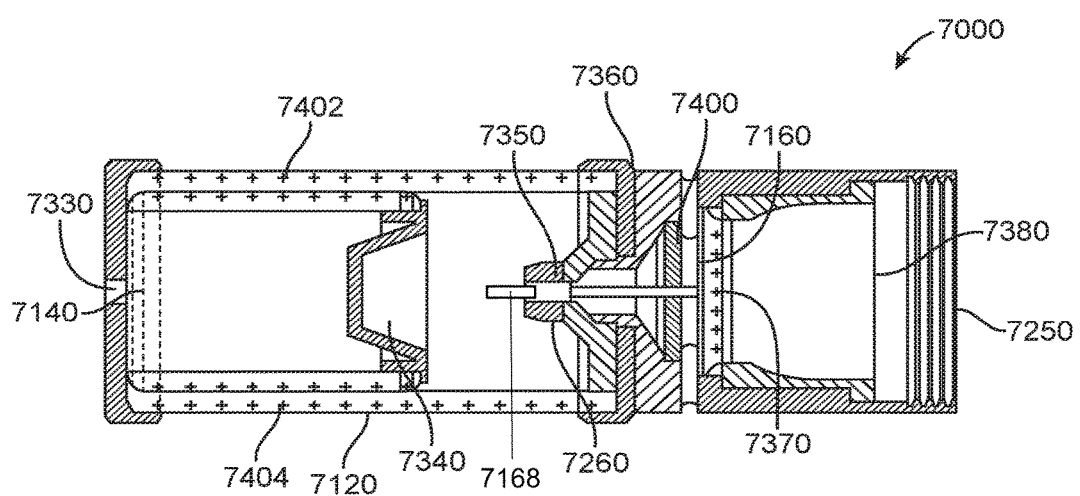
FIG. 7 shows an exemplary embodiment of a hand-held inhalable vapor generating device comprising a shuttle plug.

FIGS. 7A-7C show an exemplary embodiment of a device 7000 comprising a shuttle plug 7140. In some of these embodiments of the cartridge 7120, a plunger comprises a shuttle plug 7140 which comprises a piston-shaped body that in some embodiments has a hollow air-filled interior.

A cartridge 7120 is configured to contain a substance to be vaporized or aerosolized 7150 and to deliver the substance to be vaporized or aerosolized 7150 to one or more channels within the thermal valve assembly 7160. In some embodiments of the systems, devices, and methods described herein, the cartridge 7120 further contains a shuttle plug 7140, and in some embodiments of the systems, devices, and methods described herein, a cartridge 7120 contains a shuttle plug spring 7130. In some embodiments of the systems, devices, and methods described herein, a shuttle plug 7140 is positioned within a cartridge 7120 so that the shuttle plug 7140 is proximal to the user relative to the substance to be vaporized or aerosolized 7150 when the mouthpiece 7110 of the device 7000 is oriented towards the user's mouth. In these embodiments, the shuttle plug 7140 is thus positioned to push the substance to be vaporized or aerosolized 7150 out of the cartridge 7120 distally relative to a position of a user. It should be understood, however, that multiple configurations and orientations of the components within the cartridge 7120 are also suitable for use with the systems, devices, and methods described herein. For example, in some embodiments of the systems, devices, and methods described herein, the shuttle plug is positioned distally to a user relative to the position of a substance to be vaporized or aerosolized 7150 when the mouthpiece 7110 is oriented towards the user's mouth. In some embodiments of the systems, devices, and methods described herein, for example, the cartridge 7120 is not positioned within the mouthpiece 7110.

In some embodiments of the systems, devices, and methods described herein, a shuttle plug 7140, within a cartridge 7120, is positioned so that the shuttle plug 7140 abuts the substance to be vaporized or aerosolized 7150, and is further configured so that as the substance to be vaporized or aerosolized 7150 advances out of the cartridge 7120, the shuttle plug 7140 advances in a distal direction relative to a user when the mouthpiece 7110 of the device 7000 is oriented towards a user's mouth. In some embodiments of the systems, devices, and methods described herein, the shuttle plug 7140 is advanced within the cartridge 7120 by a shuttle plug spring 7130. In some embodiments of the systems, devices, and methods described herein, a shuttle plug spring 7130 is in operative communication with the shuttle plug 7140 so that the shuttle plug spring 7130 conveys a force to the shuttle plug 7140, thereby causing the shuttle plug 7140 to advance and push the substance to be vaporized or aerosolized 7150 into one or more channels within the thermal valve assembly 7160.

In some embodiments of the systems, devices, and methods described herein, one or more of the outer surface of the shuttle plug 7140 and the inner surface of the cartridge 7120 comprises a material that creates a frictionless movement of the shuttle plug 7140 within the cartridge 7120. For example, in some embodiments of the systems, devices, and methods described herein, the shuttle plug 7140 has an outer surface made of glass and the cartridge 7120 has an inner surface made of glass. In some of these embodiments, having two glass surfaces, a thin layer of liquid 7402 and 7404 is between the glass surface of the shuttle plug 7140 and the glass inner surface of the cartridge 7120 so that the shuttle plug 7140 moves frictionlessly against the glass inner surface of the cartridge 7120. In some of these embodiments, having two glass surfaces, the cartridge 7120 does not include a shuttle plug spring 7130. In some of these embodiments, having two glass surfaces, the thin layer of fluid between the shuttle plug 7140 and the cartridge 7120 is the substance to be vaporized or aerosolized.

In some embodiments of the systems, devices, and methods described herein, a shuttle plug 7140 is advanced against a substance to be vaporized or aerosolized 7150 when a user engages the mouthpiece 7110 and withdraws vapor, creating a suction force that advances the shuttle plug against the substance to be vaporized or aerosolized 7150, and thereby pushes the substance to be vaporized or aerosolized 7150 out of the cartridge 7120, through an opening 7350 in the cartridge 7120, and into one or more channels (not shown) within a thermal valve assembly 7160.

In some embodiments of the systems, devices, and methods described herein, a cartridge 7120 comprises a bag (not shown) or balloon that advances the substance to be vaporized or aerosolized 7150 out of the one or more channels rather than a shuttle plug 7140. In these embodiments, the substance to be vaporized or aerosolized 7150 is positioned within the bag or balloon so that when the bag or balloon either compresses or is advanced against the substance to be vaporized or aerosolized 7150, the substance to be vaporized or aerosolized 7150 is advanced through the opening 7350, out of the cartridge 7120, and into one or more channels (not shown) within a thermal valve assembly 7160.

Figure 8:
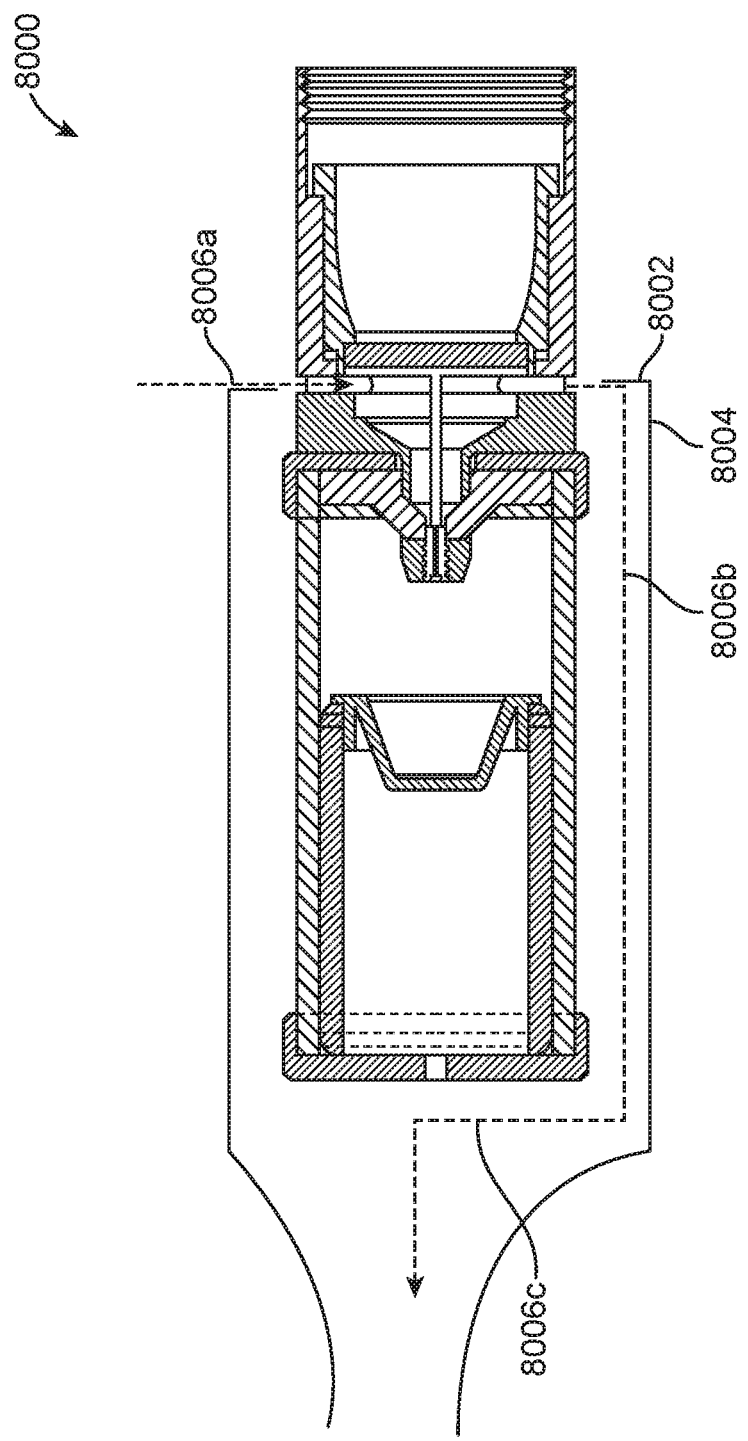
FIG. 8 shows an illustration of an exemplary pathway of a vapor or aerosol stream through a hand-held inhalable vapor generating device.

FIG. 8 shows an illustration of an exemplary pathway of a vapor or aerosol stream 8006a-80006c through a device 8000, which may comprise hand-held inhalable vapor generating device. A pathway of a generated vapor or aerosol through the device 8000 initially begins with a flow of air entering the device 8000 through a side port (not shown) of the device 8000. Air flow through a device 8000, in some embodiments of the systems, devices, and methods described herein, is initiated by a user drawing air through the device by creating a suction force through the mouthpiece using his or her mouth (i.e., by sucking in air through the mouthpiece). The airflow into the device 8000 mixes with a generated vapor or aerosol within the device to become a mixed flow 8006a. In some embodiments, a mixed flow 8006a contains particles of the substance to be vaporized and aerosolized having a relatively homogenous composition. In some embodiments, a mixed flow 8006a contains particles of the substance to be vaporized and aerosolized having a relatively heterogeneous composition. As the mixed flow 8006a travels through the device 8000, the mixed flow 8006a encounters the mouthpiece 8002 and, in particular, collides with impact wall 8004 of the mouthpiece 8002. The impact wall 8004 is positioned so that it is essentially perpendicular to the direction of flow of the mixed flow 8006a. At the point of impact of the mixed flow 8006a with the impact wall, a portion of the mixed flow 8006b navigates the essentially 90 degree turn that the flow must make due to the impact wall 8004. In general, a portion of the mixed flow 8006a that comprises larger particles will not navigate the essentially 90 degree turn at the impact wall 8004 and will deposit there rather than continue with the portion of the mixed flow 8006b towards the mouth of the user. As the flow continues towards the mouth of the user, it further navigates additional turns within the mouthpiece 8002 and likewise, relatively larger particles are shed from the portion of mixed flow 8006b along the way as the larger particles are unable to navigate the additional turns. As a result, an inhaled flow 8006c is generated in which the vapor or aerosol within the flow has become a much more homogenous mixture in terms of particle size along the way with the shedding of relatively larger particles. Because, in general, larger particles tend to be contaminants within the flow of vapor or aerosol, the passage of the vapor and aerosol from 8006a to 8006c through the device 8000 tends to purify the vapor or aerosol of contaminants before it reaches the mouth and airway of a user.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A hand-held inhalable vapor producing device comprising:
    a cartridge with an opening, the cartridge containing a liquid;
    a channel outside of the cartridge, continuous with the opening, and positioned to receive the liquid from the cartridge;
    a thermal valve having a first conformation that seals the opening and a second conformation that unseals the opening to enable liquid to flow from the cartridge, through the opening, and into the channel;
    a conducting plate in fluid communication with the channel, the conducting plate including a plurality of pores that receive the liquid flowing into the channel; and
    a heat source in thermal communication with the thermal valve and the conducting plate.

2. The hand-held inhalable vapor producing device of claim 1, wherein the cartridge includes an ejector that can advance the liquid through the opening and into the channel when the thermal valve is in the second conformation.

3. The hand-held inhalable vapor producing device of claim 2, wherein the ejector travels frictionlessly within the cartridge.

4. The hand-held inhalable vapor producing device of claim 3, wherein the cartridge and the ejector are made of glass.

5. The hand-held inhalable vapor producing device of claim 1, wherein the cartridge is removable from a remainder of the hand-held inhalable vapor producing device.

6. The hand-held inhalable vapor producing device of claim 1, wherein the cartridge includes a bag that opens to the opening and the liquid is located within an interior of the bag.

7. The hand-held inhalable vapor producing device of claim 6, wherein the bag is positioned to advance the liquid through the opening and into the channel when the thermal valve is in the second conformation.

8. The hand-held inhalable vapor producing device of claim 1, wherein the liquid comprises nicotine.

9. The hand-held inhalable vapor producing device of claim 1, wherein a size of the channel enables capillary action to advance liquid through the channel.

10. The hand-held inhalable vapor producing device of claim 1, wherein the thermal valve changes from the first conformation to the second conformation upon actuation of the heat source.

11. The hand-held inhalable vapor producing device of claim 10, wherein the thermal valve comprises one or more materials that change conformation when heated.

12. The hand-held inhalable vapor producing device of claim 11, wherein the thermal valve comprises a first metallic layer and a second metallic layer, the second metallic layer faces the heat source, and the second metallic layer has a higher coefficient of thermal expansion than the first metallic layer.

13. The hand-held inhalable vapor producing device of claim 12, wherein the thermal valve comprises a moveable rod that seals the opening in the first conformation and unseals the opening in the second conformation.

14. The hand-held inhalable vapor producing device of claim 1, wherein the channel has a proximal end adjacent to the cartridge and a distal end adjacent to the conducting plate, the channel widening to a reservoir at the distal end.

15. The hand-held inhalable vapor producing device of claim 14, wherein the conducting plate is positioned to receive the liquid from the reservoir.

16. The hand-held inhalable vapor producing device of claim 15, wherein the conducting plate comprises a metal.

17. The hand-held inhalable vapor producing device of claim 16, wherein the conducting plate comprises titanium.

18. The hand-held inhalable vapor producing device of claim 15, wherein the conducting plate comprises a ceramic.

19. The hand-held inhalable vapor producing device of claim 1, wherein the heat source comprises a light source.

20. The hand-held inhalable vapor producing device of claim 19, wherein the light source comprises a laser.

* * * * *